United States Patent
Džakula

(10) Patent No.: US 6,438,205 B1
(45) Date of Patent: Aug. 20, 2002

(54) SYSTEM AND METHOD FOR REDUCING PHASE AMBIGUITY OF CRYSTAL STRUCTURE FACTORS

(75) Inventor: Željko Džakula, Rancho Penasquitos, CA (US)

(73) Assignee: Accelrys Inc., San Diego, CA (US)

( * ) Notice: Subject to any disclaimer, the term of this patent is extended or adjusted under 35 U.S.C. 154(b) by 0 days.

(21) Appl. No.: 09/851,503

(22) Filed: May 8, 2001

Related U.S. Application Data

(60) Provisional application No. 60/202,834, filed on May 8, 2000.

(51) Int. Cl.⁷ .................................. G01N 23/207
(52) U.S. Cl. .................. 378/73; 378/71; 378/86
(58) Field of Search .................. 378/71, 73, 86, 378/70

(56) References Cited

U.S. PATENT DOCUMENTS

| | | | |
|---|---|---|---|
| 4,991,191 A | * | 2/1991 | Suryanarayanan .......... 250/304 |
| 5,353,236 A | | 10/1994 | Subbiah |
| 6,192,103 B1 | * | 2/2001 | Wormington et al. ......... 378/73 |

OTHER PUBLICATIONS

*An Introduction to X–Ray Crystallography*, Michael M. Woolfson, Cambridge University Press (1970, 1997), Section 8–4, pp. 255–267.
A Stochastic approach to molecular replacement, Glykos and Kokkinidis, ActaCryst., vol. 056, p. 169 (2000).
*Principles of Protein X–Ray Crystallography*, Jan Drenth, Chapter 8, pp. 183–198, Springer–Verlag, New York (1999).
PCT International Search Report for PCT/US 01/15003 filed 08/05/01, Applicant: Molecular Simulations, Inc.
Probabilistic Distribution of One–Phase Structure Seminvariants for an Isomorphous Pair of Structures: Theoretical Basis and Initial Appllictions, Liu Yongsheng, et al., Acta Cryst. (1996). vol. A52, Pt. 1 oo. 56–61.

* cited by examiner

*Primary Examiner*—David V. Bruce
*Assistant Examiner*—Pamela R. Hobden
(74) *Attorney, Agent, or Firm*—Knobbe, Martens, Olson & Bear, LLP

(57) ABSTRACT

A method reduces the structure factor phase ambiguity corresponding to a selected reciprocal lattice vector. The method includes generating an original phase probability distribution corresponding to a selected structure factor phase of the selected reciprocal lattice vector. The original phase probability distribution includes a first structure factor phase ambiguity. The method further includes combining the original phase probability distribution with a plurality of phase probability distributions of a plurality of structure factor phases of other reciprocal lattice vectors using a phase equation or inequality. The phase equation or inequality defines a mathematical relationship between the selected structure factor phase of the selected reciprocal lattice vector and the plurality of structure factor phases of other reciprocal lattice vectors. The method further includes producing a resultant phase probability distribution for the selected structure factor phase of the selected reciprocal lattice vector. The resultant phase probability distribution includes a second structure factor phase ambiguity which is smaller than the first structure factor phase ambiguity.

17 Claims, 17 Drawing Sheets

$\vec{k}-\vec{h}=(2,2,0)$ $\vec{k}-\vec{h}=(2,2,0)$

SYSTEM AND METHOD FOR REDUCING PHASE AMBIGUITY OF CRYSTAL STRUCTURE FACTORS

CROSS REFERENCE TO RELATED APPLICATIONS

This application claims priority under 35 U.S.C. § 119(e) to U.S. Provisional Patent Application No. 60/202,834, entitled "System and Method for Reducing Phase Ambiguity of Crystal Structure Factors" and filed May 8, 2000.

BACKGROUND OF THE INVENTION

1. Field of the Invention

This invention relates to methods and systems for determining molecular structures using x-ray crystallography.

2. Description of Related Art

In x-ray diffraction crystallography, a crystalline form of the molecule under study is exposed to a beam of x-rays, and the intensity of diffracted radiation at a variety of angles from the angle of incidence is measured. The beam of x-rays is diffracted into a plurality of diffraction "reflections," each reflection representing a reciprocal lattice vector. From the diffraction intensities of the reflections, the magnitudes of a series of numbers, known as "structure factors," are determined. The structure factors in general are complex numbers, having a magnitude and a phase in the complex plane, and are defined by the electron distribution within the unit cell of the crystal.

The magnitudes of the complex numbers are relatively easy to experimentally determine from measured diffraction intensities of the various reflections. However, a map of electron density and/or atomic position within the unit cell of the crystal cannot be generated without determining the phases of the structure factors as well. Thus, the central problem in x-ray diffraction crystallography is the determination of phases for structure factors whose amplitudes are already known.

In attempts to determine the structure of large biomolecules such as proteins, one of the most frequently used approaches to solve this problem is based on isomorphous replacement. In single isomorphous replacement (SIR) analysis, one or more heavy atoms are attached to the protein, creating a heavy atom derivative or isomorph of the protein. An analysis of the difference between the x-ray diffraction intensities from the native protein and from its heavy atom derivative can limit the phase of at least some structure factors to two plausible possibilities. For each structure factor, this SIR analysis results in a phase probability distribution curve which is typically substantially bimodal, with peaks positioned at the two most probable phases for that structure factor.

To remove the ambiguity of which probability peak corresponds to the correct phase for each structure factor, a plurality of heavy atom derivatives can be used to generate a set of phase probability distribution curves for each structure factor. In this multiple isomorphous replacement (MIR) analysis, the probability distribution curves for a selected structure factor are mathematically combined such that the resulting phase value is consistent across all of the heavy atom derivatives for the selected structure factor. In essence, the resulting phase value common to the set of phase probability distribution curves corresponds to the correct phase of the structure factor. An alternative analysis, multiple anomalous diffraction (MAD) has mathematical formalisms which are similar to those of MIR analysis. Aspects of these two procedure are described in Section 8.4, pages 255–267, of *An Introduction to X-Ray Crystallography* by Michael M. Woolfson, Cambridge University Press (1970, 1997). The complete content of the Woolfson textbook is hereby incorporated by reference in its entirety.

The heavy atom derivative method is commonly used when the structure of the protein or other molecule(s) in the unit cell is wholly unknown. However, the preparation of heavy atom derivatives is slow and tedious, and the creation of a sufficient number of heavy atom isomorphs to sufficiently reduce the phase ambiguity is not always possible.

SUMMARY OF THE INVENTION

According to one aspect of the present invention, a method reduces the structure factor phase ambiguity corresponding to a selected reciprocal lattice vector. The method comprises generating an original phase probability distribution corresponding to a selected structure factor phase of the selected reciprocal lattice vector. The original phase probability distribution comprises a first structure factor phase ambiguity. The method further comprises combining the original phase probability distribution with a plurality of phase probability distributions of a plurality of structure factor phases of other reciprocal lattice vectors using a phase equation or inequality. The phase equation or inequality defines a mathematical relationship between the selected structure factor phase of the selected reciprocal lattice vector and the plurality of structure factor phases of other reciprocal lattice vectors. The method further comprises producing a resultant phase probability distribution for the selected structure factor phase of the selected reciprocal lattice vector. The resultant phase probability distribution comprises a second structure factor phase ambiguity which is smaller than the first structure factor phase ambiguity.

According to another aspect of the present invention, a method defines a structure factor phase for a reflection derived from x-ray crystallography data. The method comprises generating a first probability distribution for the structure factor phase of the reflection. The method further comprises generating two or more additional probability distributions for the structure factor phases of other reflections. The method further comprises calculating a composite probability distribution for the structure factor phase of the reflection. The composite probability distribution is derived from the first probability distribution of the reflection and the two or more additional probability distribution of the other reflections.

According to another aspect of the present invention, the methods described herein are implemented on computer readable medium having instructions stored thereon which causes a general purpose computer system to perform the methods described herein. According to another aspect of the present invention, a computer-implemented x-ray crystallography analysis system is programmed to perform the methods described herein.

According to another aspect of the present invention, a computer-implemented x-ray crystallography analysis system comprises a means for retreiving a first phase probability distribution corresponding to a selected structure factor phase of a selected reciprocal lattice vector. The system further comprises a means for retreiving a plurality of second phase probability distributions corresponding to other structure factor phases of other reciprocal lattice vectors. The system further comprises a means for combining the first phase probability distribution and plurality of second phase probability distributions so as to produce a resultant phase probability distribution for the selected structure factor phase of the selected reciprocal lattice vector.

According to another aspect of the present invention, a method refines x-ray diffraction data. The method comprises combining structure factor phase probability distributions for different reciprocal lattice vectors so that the structure factor phase probability distribution for at least one of the reciprocal lattice vectors is more heavily weighted toward a phase value.

DETAILED DESCRIPTION OF THE PREFERRED EMBODIMENT

In describing embodiments of the invention, the terminology used is not intended to be interpreted in any limited or restrictive manner, simply because it is being utilized in conjunction with a detailed description of certain specific embodiments of the invention. Furthermore, embodiments of the invention may include several novel features, no single one of which is solely responsible for its desirable attributes or which is essential to practicing the inventions herein described.

In many embodiments, the present invention is useful in computer-implemented x-ray crystallography analysis processes. In these processes, x-ray crystallography data is analyzed using software code running on general purpose computers, which can take a wide variety of forms, including, but not limited to, network servers, workstations, personal computers, mainframe computers, and the like. The code which configures the computer to perform these analyses is typically provided to the user on a computer readable medium, such as a CD-ROM. The code may also be downloaded by a user from a network server which is part of a local or wide-area network, such as the Internet.

The general purpose computer running the software will typically include one or more input devices such as a mouse and/or keyboard, a display, and computer readable memory media such as random access memory integrated circuits and a hard disk drive. It will be appreciated that one or more portions, or all of the code may be remote from the user and, for example, resident on a network resource such as a LAN server, Internet server, network storage device, etc. In typical embodiments, the software receives as an input a variety of information, such as the x-ray crystallographic data and any user-determined parameters for the analysis.

Figure 1:
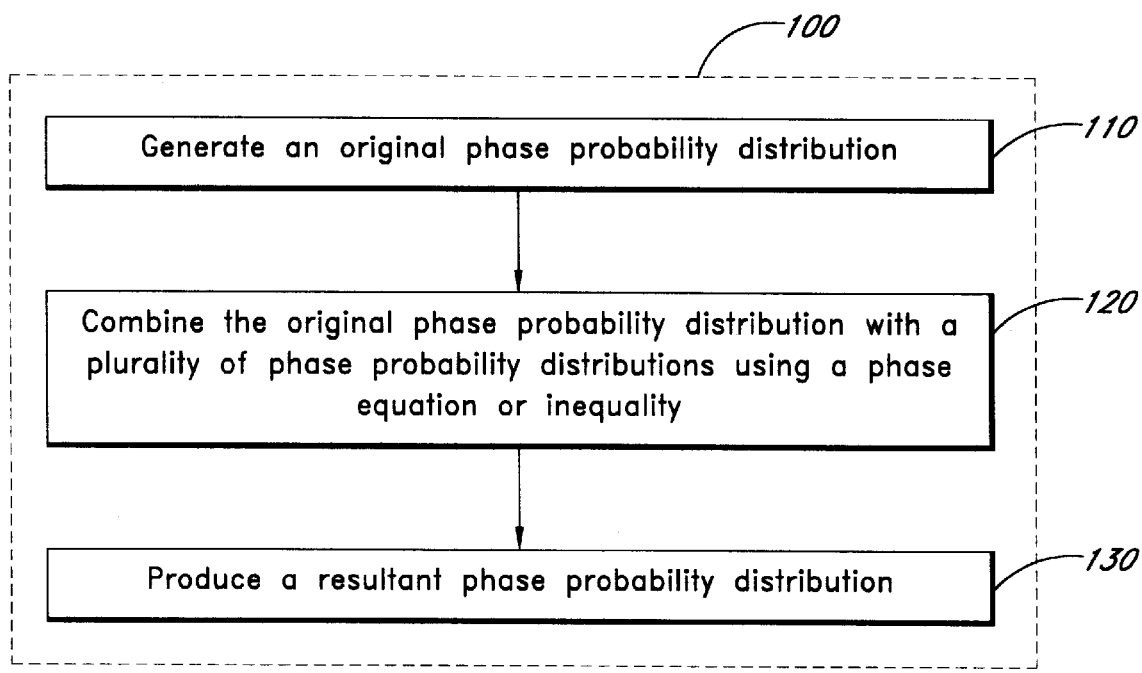
FIG. 1 is a flowchart of one embodiment of a method of reducing structure factor phase ambiguity corresponding to a selected reciprocal lattice vector.

FIG. 1 is a flowchart of one embodiment of a method 100 of reducing structure factor phase ambiguity corresponding to a selected reciprocal lattice vector. The method 100 comprises generating an original phase probability distribution in an operational block 110. The original phase probability distribution corresponds to a selected structure factor phase of the selected reciprocal lattice vector, and comprises a first structure factor phase ambiguity. The method 100 further comprises combining the original phase probability distribution with a plurality of phase probability distributions of a plurality of structure factor phases of other reciprocal lattice vectors using a phase equation or inequality in an operational block 120. The phase equation or inequality defines a mathematical relationship between the selected structure factor phase of the selected reciprocal lattice vector and the plurality of structure factor phases of other reciprocal lattice vectors. The method 100 further comprises producing a resultant phase probability distribution for the selected structure factor phase of the selected reciprocal lattice vector in an operational block 130. The resultant phase probability distribution comprises a second structure factor phase ambiguity which is smaller than the first structure factor phase ambiguity.

In the operational block 110, an original phase probability distribution is generated which corresponds to a selected structure factor phase of the selected reciprocal lattice vector. In certain embodiments, the original phase probability distribution is generated using single-isomorphous replacement (SIR) analysis. Other examples of analyses which can generate the original phase probability distribution in other embodiments include, but are not limited to single anomalous dispersion (SAD), multiple isomorphous replacement (MIR) and multiple anomalous dispersion (MAD).

As is known to those of skill in the art, the usual result of SIR analysis is a set of Hendrickson-Lattman coefficients $a_{\vec{k}}, b_{\vec{k}}, c_{\vec{k}}, d_{\vec{k}}$ for each reciprocal lattice vector $\vec{k}$. These coefficients define the original phase probability distribution $p(\Phi_{\vec{k}}, a_{\vec{k}}, b_{\vec{k}}, c_{\vec{k}}, d_{\vec{k}})$ for each corresponding structure factor according to the following standard formula:

$$p(\Phi_{\vec{k}}, a_{\vec{k}}, b_{\vec{k}}, c_{\vec{k}}, d_{\vec{k}}) = \exp[a_{\vec{k}} \cos(\Phi_{\vec{k}}) + b_{\vec{k}} \sin(\Phi_{\vec{k}}) + c_{\vec{k}} \cos(2\Phi_{\vec{k}}) + d_{\vec{k}} \sin(2\Phi_{\vec{k}})],$$

Equation 1 where $\Phi_{\vec{k}}$ corresponds to the structure factor phase of a reciprocal lattice vector $\vec{k}$, and $a_{\vec{k}}, b_{\vec{k}}, c_{\vec{k}}, d_{\vec{k}}$ correspond to the Hendrickson-Lattman coefficients for the reciprocal lattice vector $\vec{k}$. The normalization factor of Equation 1 has been omitted for simplicity.

Figure 2:
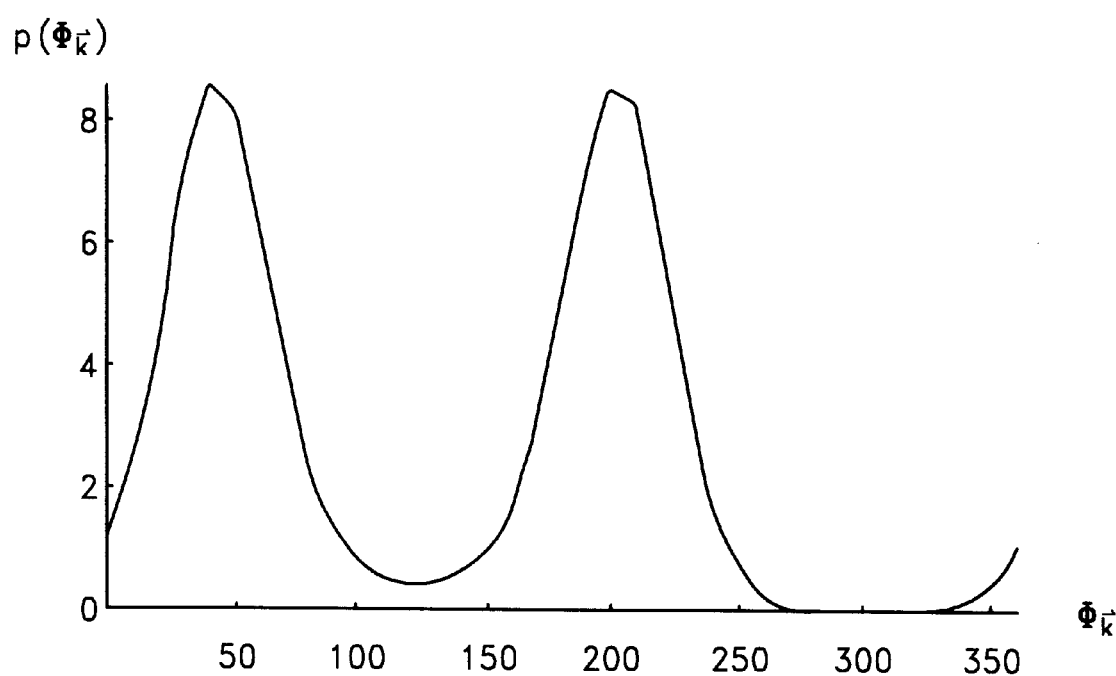
FIG. 2 schematically illustrates an example of a substantially bimodal phase probability distribution $p(\Phi_{\vec{k}})$ for the phase $\Phi_{\vec{k}}$ corresponding a reciprocal lattice vector $\vec{k}$.

As described above, the shapes of the phase probability distributions generated from SIR analysis are generally bimodal (i.e., the distribution has two prominent probability modes). In such a bimodal phase probability distribution, the phase has a significant likelihood of being in either mode of the distribution. An example of a substantially bimodal phase probability distribution $p(\Phi_{\vec{k}})$ is illustrated in FIG. 2 for the phase $\Phi_{\vec{k}}$ corresponding to a reciprocal lattice vector $\vec{k}$. The phase probability distribution $p(\Phi_{\vec{k}})$ in FIG. 2 has a mode centered at approximately 30 degrees and a second, approximately equal mode at approximately 170 degrees. The value of the phase $\Phi_{\vec{k}}$ then has an approximately equal probability of being either approximately 30 degrees or approximately 170 degrees. The structure factor phase ambiguity of a phase probability distribution can be defined in terms of the relative weight of each mode of the bimodal distribution. As illustrated in FIG. 2, the two modes of the phase probability distribution $p(\Phi_{\vec{k}})$ have approximately equal weights, so it is equally likely that the phase $\Phi_{\vec{k}}$ has a value in one mode as in the other mode. Therefore the phase probability distribution $p(\Phi_{\vec{k}})$ has a relatively high structure factor phase ambiguity. The ambiguity of a phase probability distribution can be quantified by calculating a centroid which represents the ensemble average value for the phase, and a "figure of merit" (FOM) which is a measure of the reliability of the centroid. A FOM value of zero represents complete ambiguity, and a FOM value of one represents total certainty (i.e., a sharp, single-peak phase probability distribution). The phase probability distribution schematically illustrated in FIG. 2 has a centroid of 129 degrees and a FOM value of 0.19.

In the crystallographic analysis of large molecules such as proteins, there are thousands of reciprocal lattice vectors or reflections to be examined, and thus thousands of ambiguous phase determinations defined by phase probability distributions, such as the phase probability distribution $p(\Phi_{\vec{k}})$ illustrated in FIG. 2, each comprising a structure factor phase ambiguity. As described above, MIR analysis can reduce the structure factor phase ambiguities from heavy atom derivatives by analyzing x-ray crystallography data obtained for multiple heavy atom derivatives of the molecule under study. However, the preparation of these additional heavy atom derivatives is slow and tedious, and the creation of a sufficient number of heavy atom isomorphs to sufficiently reduce the structure factor phase ambiguity is not always possible.

The preparation of these additional heavy atom derivatives can be avoided by certain embodiments of the present invention. In such embodiments, the original phase probability distribution $p(\Phi_{\vec{k}})$ is combined with a plurality of phase probability distributions of a plurality of structure factor phases of other reciprocal lattice vectors using a phase equation or inequality in the operational block 120 of FIG. 1. The phase equation or inequality defines a mathematical relationship between the selected structure factor phase of the selected reciprocal lattice vector and the plurality of structure factor phases of other reciprocal lattice vectors.

Various mathematical relationships exist between the phases and/or the amplitudes of different structure factors. Such relationships have been used in various direct methods for solving crystal structures to find the most probable structure factor phases which are consistent with the measured reflections. To date, these direct methods have found application only to solving structures for relatively small molecules, where the crystal structure includes less than about 150 non-hydrogen atoms in the asymmetric unit cell. Several such methods are described in Sections 8.6, 8.7, and 8.8 of the Woolfson reference described above. Embodiments of the present invention differ from the direct methods by using experimentally determined phase probability distributions as inputs (e.g., from MIR, MAD, SIR, SAD analyses). The direct methods utilize only structure factor amplitudes as inputs.

In certain embodiments of the present invention, these mathematical relationships may be used to reduce the structure factor phase ambiguity present in the x-ray crystallography data for large molecules, such as proteins having hundreds or thousands of non-hydrogen atoms per unit cell. In certain embodiments, the phase equation or inequality can define a mathematical relationship known as the phase addition relationship:

$$\Phi_{\vec{k}} + \Phi_{-\vec{h}} = \Phi_{\vec{k}-\vec{h}}$$

Equation 2 where $\Phi_{\vec{k}}$ is the structure factor phase for the reciprocal lattice vector $\vec{k}$, $\Phi_{-\vec{h}}$ is the structure factor phase for the reciprocal lattice vector $-\vec{h}$, and $\Phi_{\vec{k}-\vec{h}}$ is the structure factor phase for the reciprocal lattice vector $\vec{k}-\vec{h}$. The phase addition relationship is based on two axioms: (1) the electron density is non-negative; and (2) the atoms are identical and discrete, with random positions in the unit cell. Certain other embodiments can utilize other phase equations or inequalities which define other mathematical relationships in accordance with the present invention. An example of another phase equation or inequality is described more fully below.

As applied to bimodal phase probability distributions, if three bimodal phase probability distributions for reciprocal lattice vectors $\vec{k}, -\vec{h}$, and $\vec{k}-\vec{h}$ have been generated, the most probable phase for reciprocal lattice vector $\vec{k}$ is the one which adds to a likely correct phase from the phase probability distribution for reciprocal lattice vector $-\vec{h}$ to produce a likely correct phase from the phase probability distribution for reciprocal lattice vector $\vec{k}-\vec{h}$.

Figure 3A:
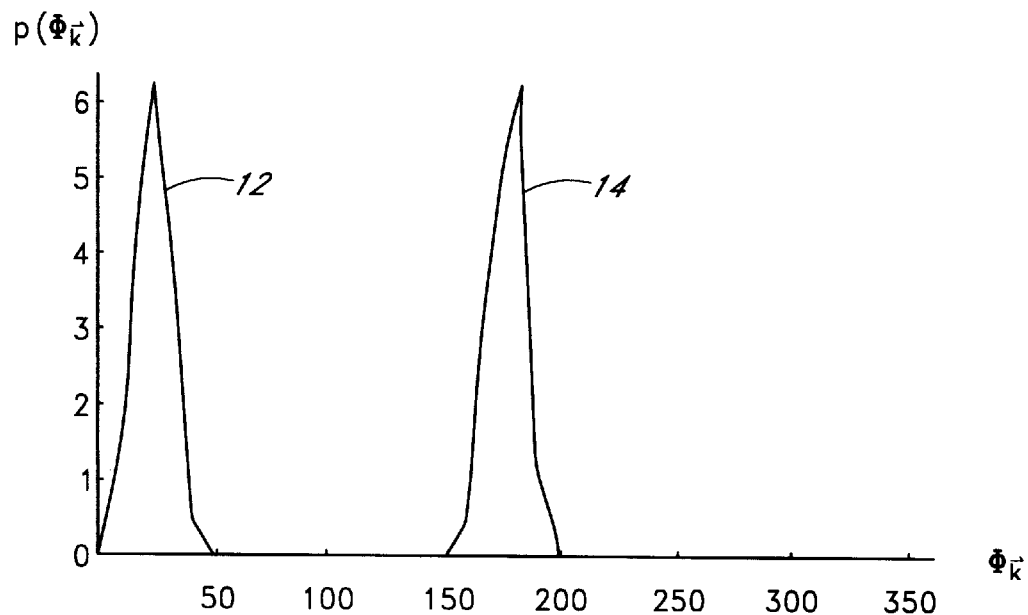
FIGS. 3A–3C schematically illustrate phase probability distributions $p(\Phi_{\vec{k}})$, $p(\Phi_{-\vec{h}})$ and $p(\Phi_{\vec{k}}-\vec{k})$ for reciprocal lattice vectors $\vec{k}$, $\vec{h}$, and $\vec{k}-\vec{h}$, respectively.
Figure 3B:
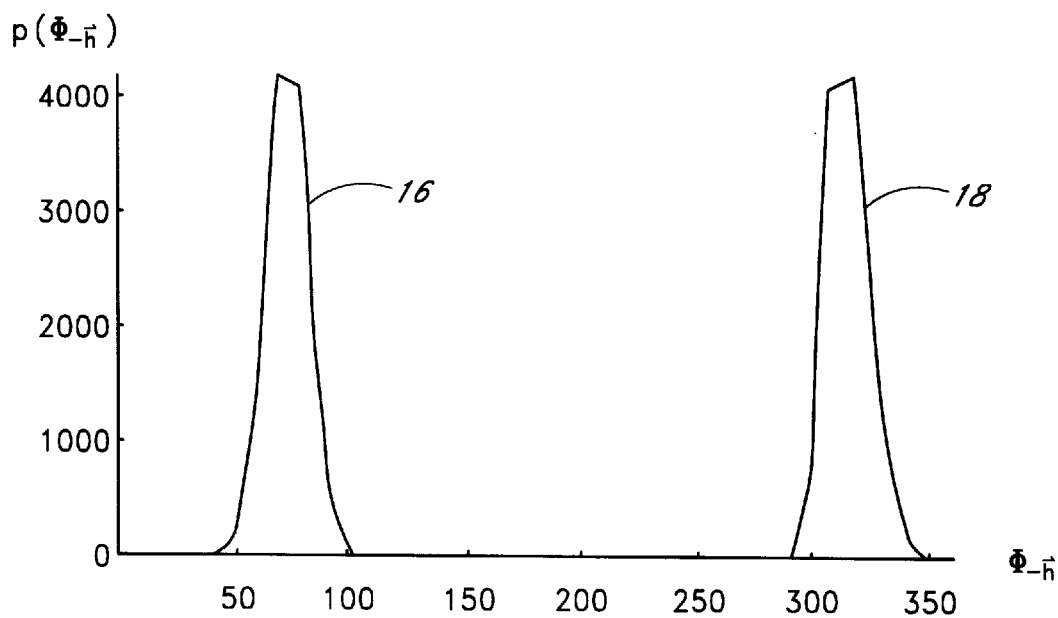
Figure 3C:
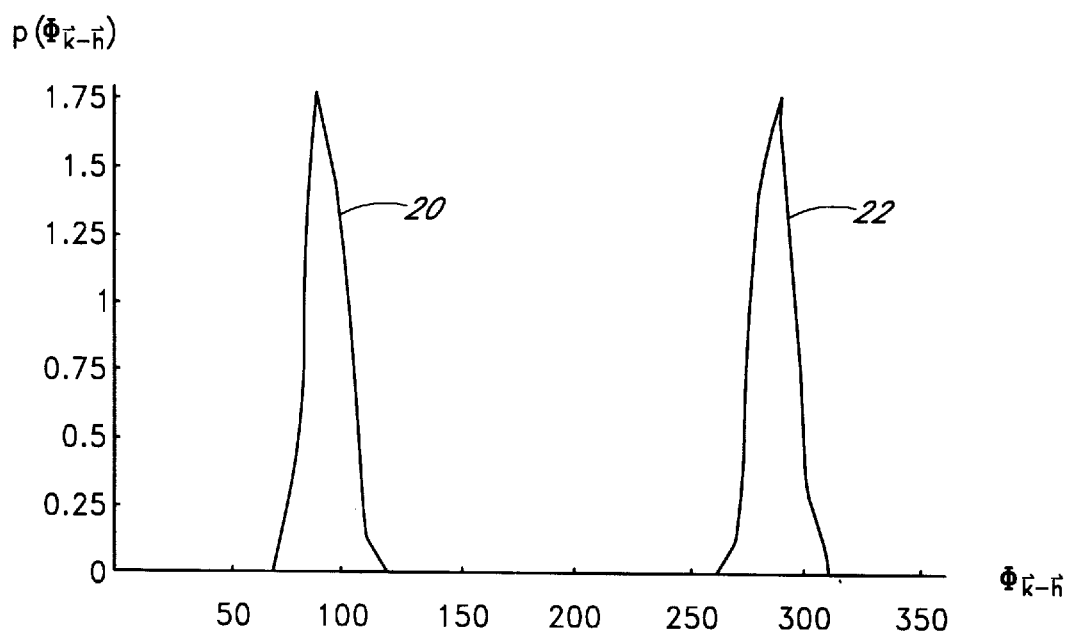

FIGS. 3A–3D schematically illustrate the combination of an original phase probability distribution $p(\Phi_{\vec{k}})$ with the phase addition relationship between a selected structure factor phase of a selected reciprocal lattice vector $\vec{k}$ and a set of structure factor phases of other reciprocal lattice vectors. FIGS. 3A–3C schematically illustrate three bimodal phase probability distributions for reciprocal lattice vectors $\vec{k}, -\vec{h}$, and $\vec{k} - \vec{h}$. The phase probability distributions of FIGS. 3A–3C have been generated synthetically to provide well-resolved mode peaks which can be easily resolved by visual analysis for illustration purposes. Such synthetically-generated functions can imitate the ambiguity found in x-ray crystallography data.

In FIG. 3A, the phase probability distribution $p(\Phi_{\vec{k}})$ for reciprocal lattice vector $\vec{k}$ has two mode peaks, a peak 12 centered at 30 degrees, and an approximately equal peak 14 centered at 170 degrees. In FIG. 3B, the phase probability distribution $p(\Phi_{-\vec{h}})$ for reciprocal lattice vector $-\vec{h}$ has two mode peaks, a peak 16 centered at 60 degrees, and a peak 18 centered at 330 degrees, and in FIG. 3C, the phase probability distribution $p(\Phi_{\vec{k}-\vec{h}})$ for reciprocal lattice vector $\vec{k} - \vec{h}$ also has two mode peaks, a peak 20 centered at 90 degrees, and a peak 22 centered at 170 degrees. The phase addition relationship implies that the true phase from reciprocal lattice vector $\vec{k}$ should add to the true phase of reciprocal lattice vector $-\vec{h}$ to produce the true phase of reciprocal lattice vector $\vec{k} - \vec{h}$. Examination of the peaks in FIGS. 3A–3C shows that the phase of peak 12 for reciprocal lattice vector $\vec{k}$ plus the phase of peak 16 for reciprocal lattice vector $-\vec{h}$ produces the phase of peak 20 for reciprocal lattice vector $\vec{k} - \vec{h}$. Thus, consistency between the phases of these reciprocal lattice vectors selects peak 12 at about 30 degrees as the correct phase for reciprocal lattice vector $\vec{k}$.

In certain embodiments, the combination of the original phase probability distribution $p(\Phi_{\vec{k}})$ with the phase equation defining the phase addition relationship in the operational block 120 of FIG. 1 is performed in a more mathematically robust and accurate manner by combining the phase addition relationship with the Hendrickson-Lattman formula as follows:

$$P(\Phi_{\vec{k}}) = p(\Phi_{\vec{k}}, a_{\vec{k}}, b_{\vec{k}}, c_{\vec{k}}, d_{\vec{k}}) \int_0^{2\pi} d p(\Phi_{-\vec{h}}, a_{-\vec{h}}, b_{-\vec{h}}, c_{-\vec{h}}, d_{-\vec{h}})$$
$$p(\Phi_{\vec{k}} + \Phi_{-\vec{h}}, a_{\vec{k}-\vec{h}}, b_{\vec{k}-\vec{h}}, c_{\vec{k}-\vec{h}}, d_{\vec{k}-\vec{h}})$$

Equation 3 where $P(\Phi_{\vec{k}})$ is a resultant phase probability distribution for the selected structure factor phase of the selected reciprocal lattice vector $\vec{k}$. Equation 3 statistically combines the phase addition relationship with the original phase probability distribution for reciprocal lattice vector $\vec{k}$ to produce a resultant probability distribution $P(\Phi_{\vec{k}})$ for the structure factor phase corresponding to reciprocal lattice vector $\vec{k}$. As described below, in other embodiments the resultant phase probability distribution can be a composite probability distribution expressed in alternative forms.

In certain embodiments, in which the original phase probability distributions are of the form shown in Equation 1, producing a resultant phase probability distribution $P(\Phi_{\vec{k}})$ for the selected structure factor phase of the selected reciprocal lattice vector $\vec{k}$ in the operational block 130 comprises evaluating the integral of Equation 3 analytically. Such an analysis can yield an infinite series involving hypergeometric Bessel functions. In other embodiments, the resultant phase probability distribution $P(\Phi_{\vec{k}})$ is produced using numerical integration, in which the form of Equation 3 may be conveniently transformed into the standard form of Equation 1. In such embodiments, the resultant phase probability distribution $P(\Phi_{\vec{k}})$ for the selected structure factor phase of the selected reciprocal lattice vector $\vec{k}$ can be expressed in terms of a revised set of Hendrickson-Lattman coefficients.

Figure 3D:
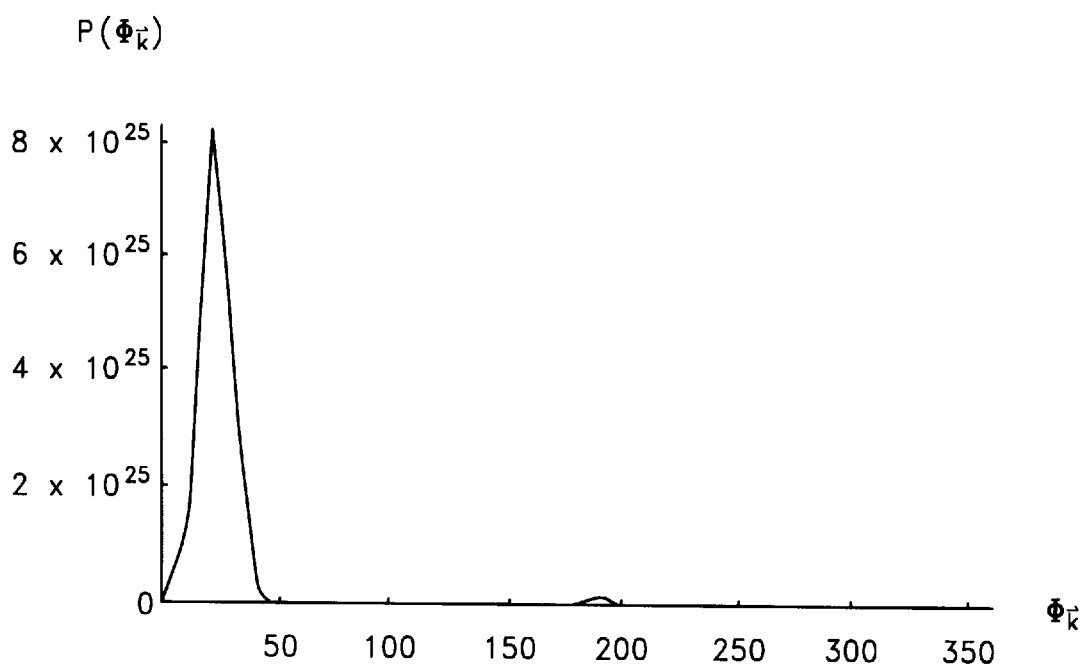
FIG. 3D schematically illustrates the resultant phase probability distribution $p(\Phi_{\vec{k}})$ for the structure factor phase corresponding to reciprocal lattice vector $\vec{k}$, based on the three phase probability distributions shown in FIGS. 3A–3C.

FIG. 3D schematically illustrates the resultant phase probability distribution $P(\Phi_{\vec{k}})$ for the structure factor phase corresponding to reciprocal lattice vector $\vec{k}$, based on the three phase probability distributions shown in FIGS. 3A–3C. The resultant phase probability distribution $p(\Phi_{\vec{k}})$ is substantially unimodal (i.e., the distribution has only one prominent probability mode). As compared to the original phase probability distribution for the reciprocal lattice vector $\vec{k}$, the resultant phase probability distribution $P(\Phi_{\vec{k}})$ has a peak 22 centered at 30 degrees, as does the original phase probability distribution $p(\Phi_{\vec{k}})$, but only has an almost completely suppressed small peak 24 at approximately 170 degrees which corresponds to second peak 14 of the original phase probability distribution $p(\Phi_{\vec{k}})$. In addition, the peak 22 of the resultant phase probability distribution $P(\Phi_{\vec{k}})$ is narrowed as compared to the corresponding peak 12 of the original phase probability distribution $p(\Phi_{\vec{k}})$.

The resultant phase probability distribution is weighted more heavily to a correct phase than is the original phase probability distribution. Because the resultant phase probability distribution $P(\Phi_{\vec{k}})$ has a larger fraction of its weight distributed among a smaller range of phases, the structure factor phase ambiguity of the resultant phase probability distribution $P(\Phi_{\vec{k}})$ is smaller than that of the original phase probability distribution $p(\Phi_{\vec{k}})$. The original phase probability distribution, as illustrated in FIG. 3A, has its centroid at 100 degrees (far away from the true value of 30 degrees) and a FOM value of 0.23. However, the resultant phase probability distribution, as illustrated in FIG. 3D, has its centroid at 28 degrees, and a FOM value of 0.92. Therefore, the resultant phase probability distribution has a smaller ambiguity than does the original phase probability distribution.

Figure 4A:
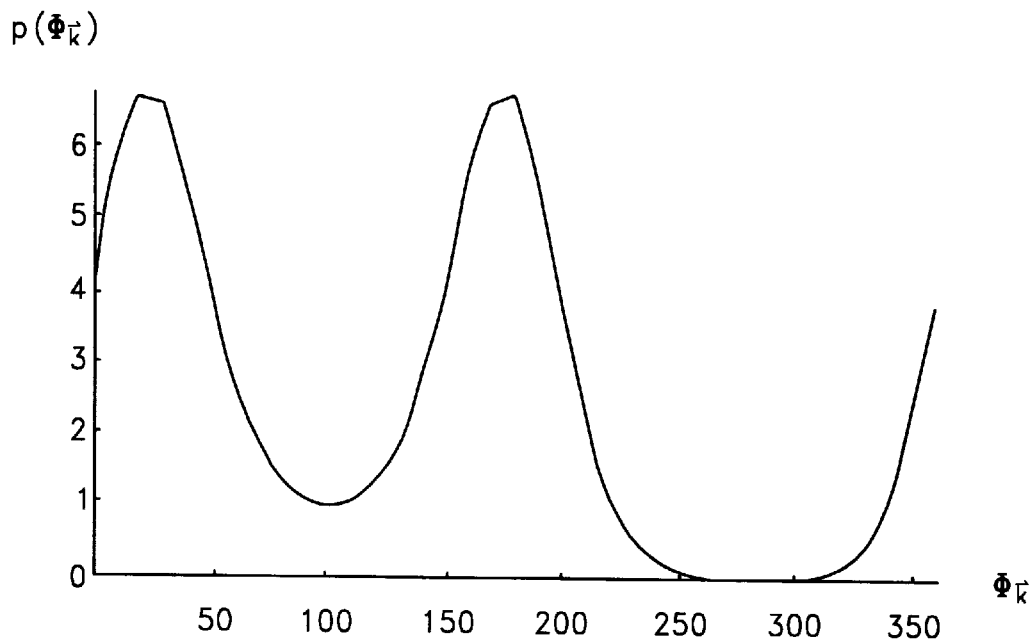
FIGS. 4A–4C schematically illustrate phase probability distributions $p(\Phi_{\vec{k}})$ $p(\Phi_{-\vec{h}})$, and $p(\Phi_{\vec{k}}-\vec{h})$ for reciprocal lattice vectors $\vec{k}$, $\vec{h}$, and $\vec{k}-\vec{h}$, respectively.
Figure 4B:
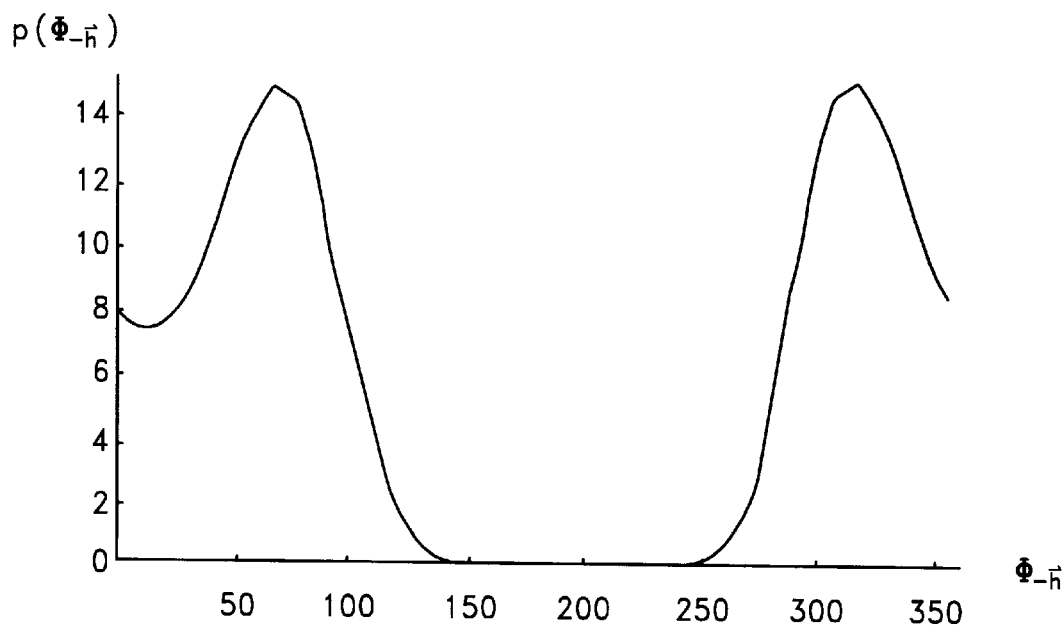
Figure 4C:
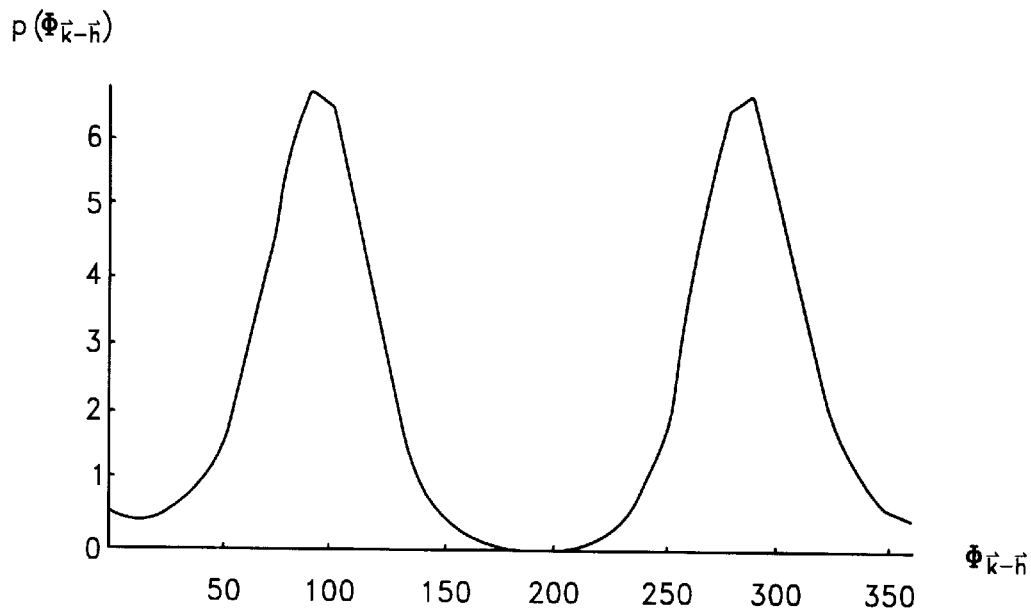
Figure 4D:
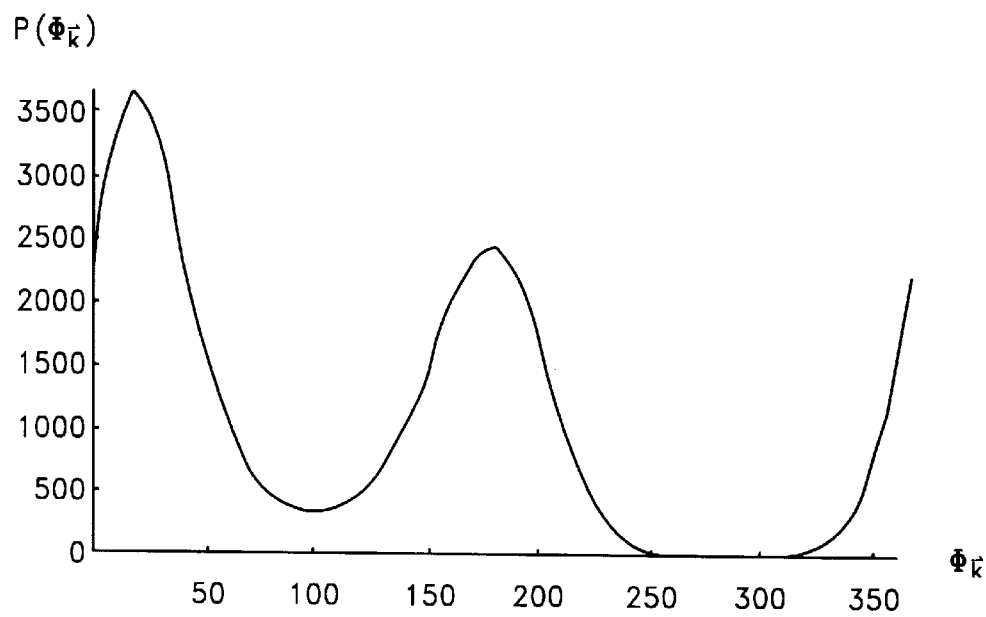
FIG. 4D schematically illustrates the resultant phase probability distribution $P(\Phi_{\vec{k}})$ for the structure factor phase corresponding to reciprocal lattice vector $\vec{k}$, based on the three phase probability distributions shown in FIGS. 4A–4C.

For embodiments in which the phase probability distributions $p(\Phi_{\vec{k}})$, $p(\Phi_{-\vec{h}})$, and $p(\Phi_{\vec{k}-\vec{h}})$ consist of wider peaks, as schematically illustrated in FIGS. 4A–4C respectively, the resultant phase probability distribution $P(\Phi_{\vec{k}})$ is still bimodal, as schematically illustrated in FIG. 4D. However, as compared to the original phase probability distribution $p(\Phi_{\vec{k}})$ of FIG. 4A, the resultant phase probability distribution $P(\Phi_{\vec{k}})$ of FIG. 4D emphasizes the correct peak mode over the incorrect peak, thereby reducing the structure factor phase ambiguity corresponding to the reciprocal lattice vector $\vec{k}$.

Despite the wider peaks of the phase probability distributions of FIGS. 4A–4C, the resultant phase probability distribution of FIG. 4D is weighted more heavily to a correct phase than is the original phase probability distribution of FIG. 4A. The original phase probability distribution, as illustrated in FIG. 4A, has its centroid at 100 degrees (far away from the true value of 30 degrees) and a FOM value of 0.28. However, the resultant phase probability distribution, as illustrated in FIG. 4D, has its centroid at 89 degrees (approximately 11 degrees closer to the true value of 30 degrees), and a FOM value of 0.27.

For essentially complete suppression of the incorrect peak mode of a bimodal original phase probability distribution, the widths of the peaks in the original phase probability distributions should be less than approximately $\Phi_{\vec{k}-\vec{h}}-(\Phi_{\vec{k}}+\Phi_{-\vec{h}})$, where $\Phi_{\vec{k}}$ and $\Phi_{-\vec{h}}$ represent the positions of the incorrect phase peak modes in the original phase probability distributions $p(\Phi_{\vec{k}})$, $p(\Phi_{-\vec{h}})$ for the reciprocal lattice vectors $\vec{k}$ and $-\vec{h}$, respectively. $\Phi_{\vec{k}-\vec{h}}$ can be the position of either the correct or incorrect phase mode for the reciprocal lattice vector $\vec{k}-\vec{h}$. Although this condition may not always be met, as schematically illustrated by the original phase probability distributions of FIGS. 4A–4C, a typical x-ray crystallography data set contains enormous numbers of redundant reciprocal lattice vector triplets. In certain embodiments, these reciprocal lattice vector triplets can be combined using a phase equation or inequality to reduce the structure factor phase ambiguity corresponding to a single reciprocal lattice vector. Typically, where the reciprocal lattice vectors are related according to their Miller indices, the structure factors are also related. In such embodiments, the cumulative analysis of multiple reciprocal lattice vector triplets as outlined above can substantially minimize the structure factor phase ambiguity even when the original phase probability distributions are extremely wide. Using multiple redundant reciprocal lattice vector triplets can produce a resultant phase probability distribution which is analogous to that produced by analyzing multiple heavy atom isomorphs. Thus, the structure factor phase ambiguity can be reduced for all reciprocal lattice vectors by scanning the entire x-ray crystallography data set for reciprocal lattice vector triplets $\vec{k}$, $-\vec{h}$, and $\vec{k}-\vec{h}$. In certain embodiments, the procedure can be iterated until a self-consistent, converged solution is found. Furthermore, in embodiments in which multiple heavy atom derivatives are available, using the above procedures improves the efficiency and accuracy of the analysis because the accuracy of the resultant phase probability distributions produced in the initial SIR analysis can be improved.

Figure 5:
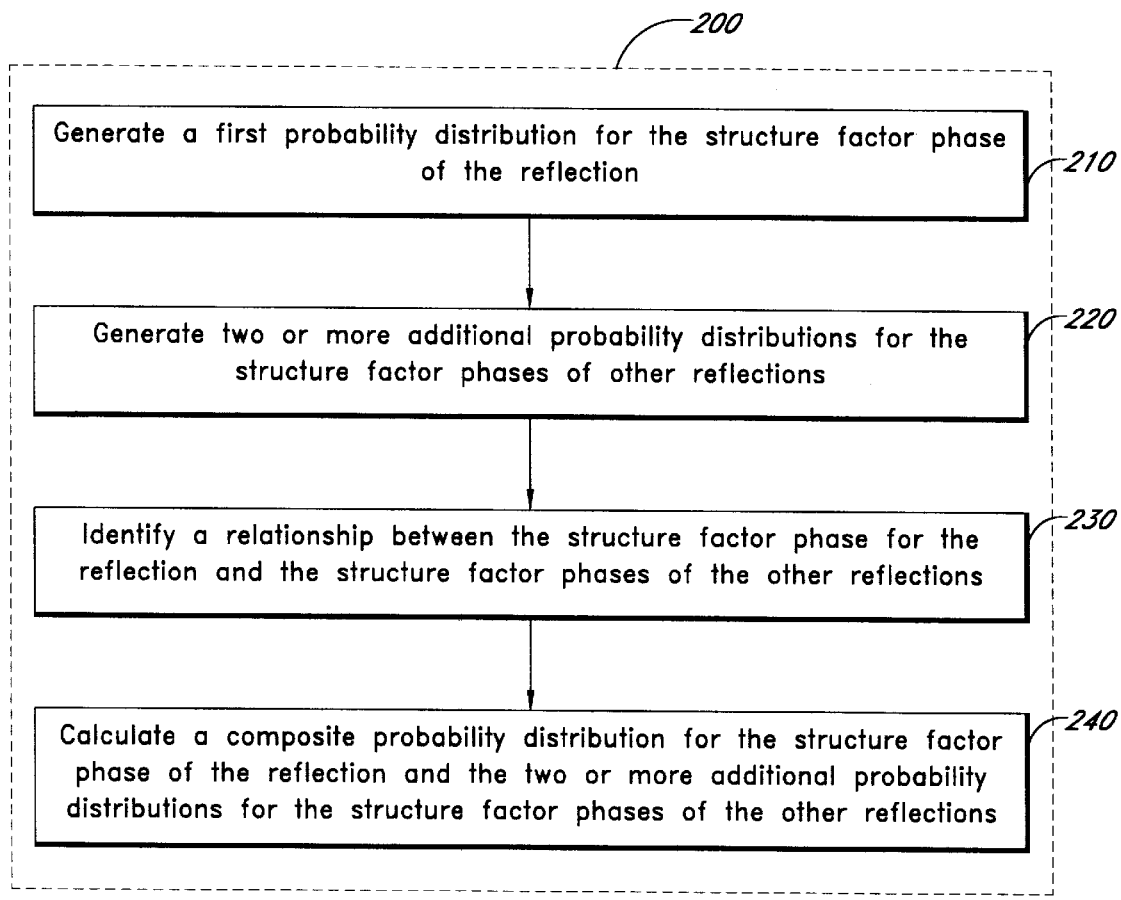
FIG. 5 is a flowchart of one embodiment of a method of defining a structure factor phase for a reflection derived from x-ray crystallography data.

FIG. 5 is a flowchart of one embodiment of a method 200 of defining a structure factor phase for a reflection derived from x-ray crystallography data. The method 200 comprises generating a first probability distribution for the structure factor phase of the reflection in an operational block 210. The method 200 further comprises generating two or more additional probability distributions for the structure factor phases of other reflections in an operational block 220. The method 200 further comprises identifying a relationship between the structure factor phase for the reflection and the structure factor phases of the other reflections in an operational block 230. The method 200 further comprises calculating a composite probability distribution for the structure factor phase of the reflection in an operational block 240. The composite probability distribution is derived from the first probability distribution for the structure factor phase of the reflection and the two or more additional probability distributions for the structure factor phases of the other reflections.

In certain embodiments, generating the first probability distribution for the structure factor phase of the reflection of the operational block 210 is performed as described above. Similarly, generating two or more additional probability distributions for the structure factor phases of other reflections of the operational block 220 is performed as described above.

In certain embodiments, identifying the relationship between the structure factor phase for the reflection and the structure factor phases of the other reflections of the operational block 230 is performed by identifying a phase equation or inequality as described above. For example, the relationship can be identified to be the phase addition relationship expressed by Equation 2. Alternatively, in other embodiments, the relationship between structure factor phases can be expressed by the so-called tangent formula:

$$tg(\Phi_{\vec{h}}) = \frac{\sum_{\vec{k}} |E_{-\vec{h}} E_{\vec{k}} E_{\vec{k}-\vec{h}}| \sin(\Phi_{\vec{k}} + \Phi_{\vec{k}-\vec{h}})}{\sum_{\vec{k}} |E_{-\vec{h}} E_{\vec{k}} E_{\vec{k}-\vec{h}}| \cos(\Phi_{\vec{k}} - \Phi_{\vec{k}-\vec{h}})} \quad \text{Equation 4}$$

where $E_{\vec{k}}$ represents the structure factor $F_{\vec{k}}$ in which the scattering factor has been set to one. Equation 4 is based on the assumption that $$\sum_{\vec{k}} E_{-\vec{h}} E_{\vec{k}} E_{\vec{k}-\vec{h}}$$

has vanishing phase, and that $$\sum_{\vec{k}} |E_{-\vec{h}} E_{\vec{k}} E_{\vec{k}-\vec{h}}| \sin(\Phi_{-\vec{h}} + \Phi_{\vec{k}} + \Phi_{\vec{k}-\vec{h}}) = 0.$$

In certain embodiments, calculating the composite probability distribution for $|E_{-\vec{h}} E_{\vec{k}} E_{\vec{k}-\vec{h}}| \sin(101_{-\vec{h}} + \Phi_{\vec{k}} + \Phi_{\vec{k}-\vec{h}}) = 0$. the structure factor phase of the reflection of the operational block 240 is performed by combining the original phase probability distribution with a phase equation or inequality and producing a resultant phase probability distribution as described above. For example, the phase addition relationship of Equation 2 can be combined with the original phase probability distribution, thereby producing Equation 3 for the resultant phase probability distribution which can be solved. Alternatively, in other embodiments in which the relationship between structure factor phases is provided by the tangent formula of Equation 4, the composite probability distribution can be expressed in the following form:

$$P(\Phi_{\vec{h}}) = p_{\vec{h}}(\Phi_{\vec{h}}) \left( \prod_i \int_0^{2\pi} d\Phi_{\vec{k}_i} \int_0^{2\pi} d\Phi_{\vec{k}_i - \vec{h}} \right) \quad \text{Equation 5}$$

$$\left( \prod_i p_{\vec{k}_i}(\Phi_{\vec{k}_i}) p_{\vec{k}_i - \vec{h}}(\Phi_{\vec{k}_i - \vec{h}}) \right) \times \delta$$

$$\left( \Phi_{\vec{h}} - \text{arctg} \frac{\sum_i |E_{\vec{k}_i} E_{\vec{k}_i - \vec{h}}| \sin(\Phi_{\vec{k}_i} + \Phi_{\vec{k}_i - \vec{h}})}{\sum_i |E_{\vec{k}_i} E_{\vec{k}_i - \vec{h}}| \cos(\Phi_{\vec{k}_i} + \Phi_{\vec{k}_i - \vec{h}})} \right)$$

where $P(\Phi_{\vec{h}})$ is the composite probability distribution and $\delta(x)$ is the delta function. In certain embodiments, the delta function can be replaced by a Gaussian function to account for experimental errors, errors in the model, and missing reflections.

In certain embodiments, the composite probability distribution is calculated in the operational block 240 by minimizing a penalty function based on the tangent formula and the probability distributions for the structure factor phases. The penalty function of certain embodiments has the following form:

$$E = \left[\sum_k |E_k E_{k-h}| \sin(\Phi_k + \Phi_{k-h}) - \text{tg}(\Phi_h) \sum_k |E_k E_{k-h}| \cos(\Phi_k + \Phi_{k-h})\right]^2 - $$
$$K_2 \sum_k [a_h \cos(\Phi_h) + b_h \sin(\Phi_h) + c_h \cos(2\Phi_h) + d_h \sin(2\Phi_h)]$$

Equation 6

In certain embodiments, Monte Carlo techniques can be utilized to start from an initial guess for a set of structure factor phases. The Monte Carlo techniques are related to those used in simulations of annealing procedures, as described by Glykos and Kokkinidis in Acta Cryst., Vol. D56, page 169, (2000), which is incorporated by reference herein in its entirety. In other embodiments, other optimization techniques can be used.

Figure 6A:
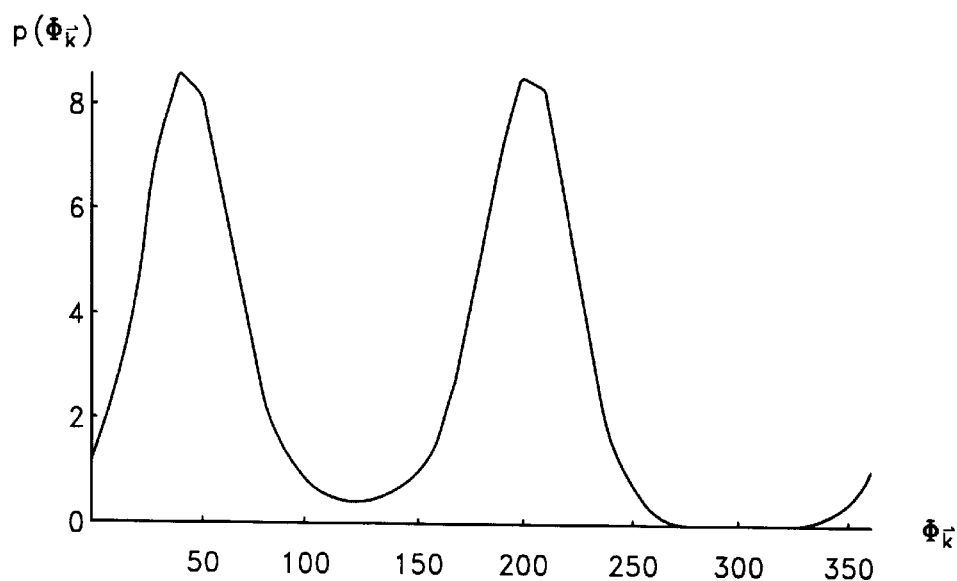
FIGS. 6A–6D schematically illustrate an example of an embodiment of the present invention as applied to certain reflections of experimental data.
Figure 6B:
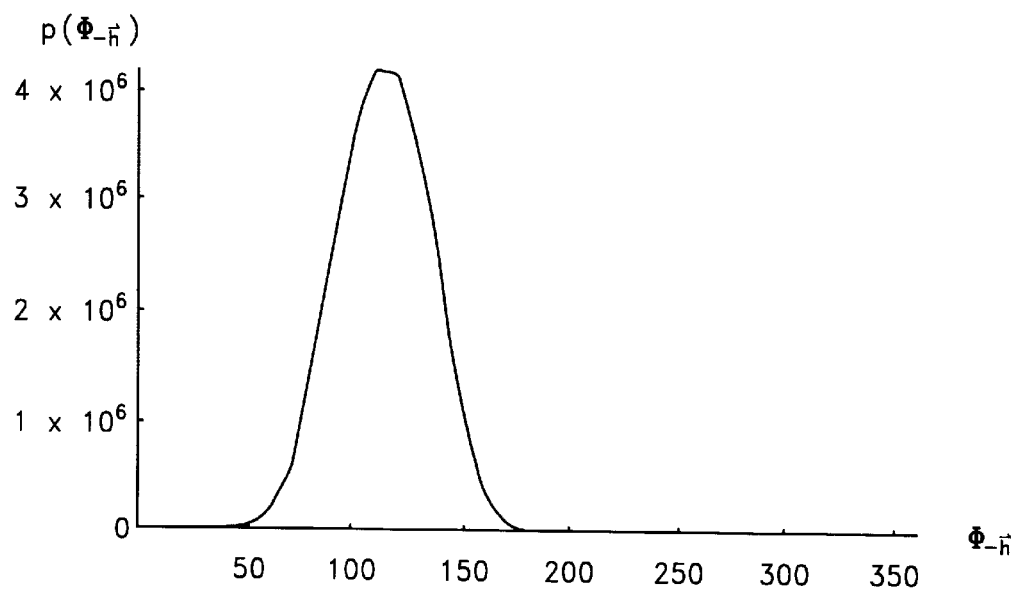
Figure 6C:
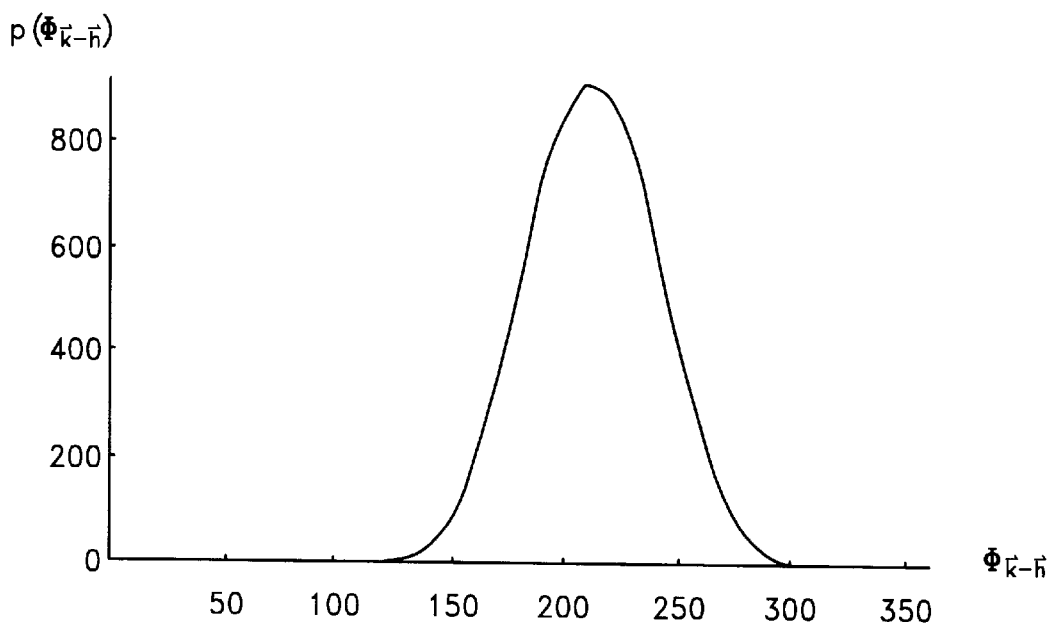
Figure 6D:
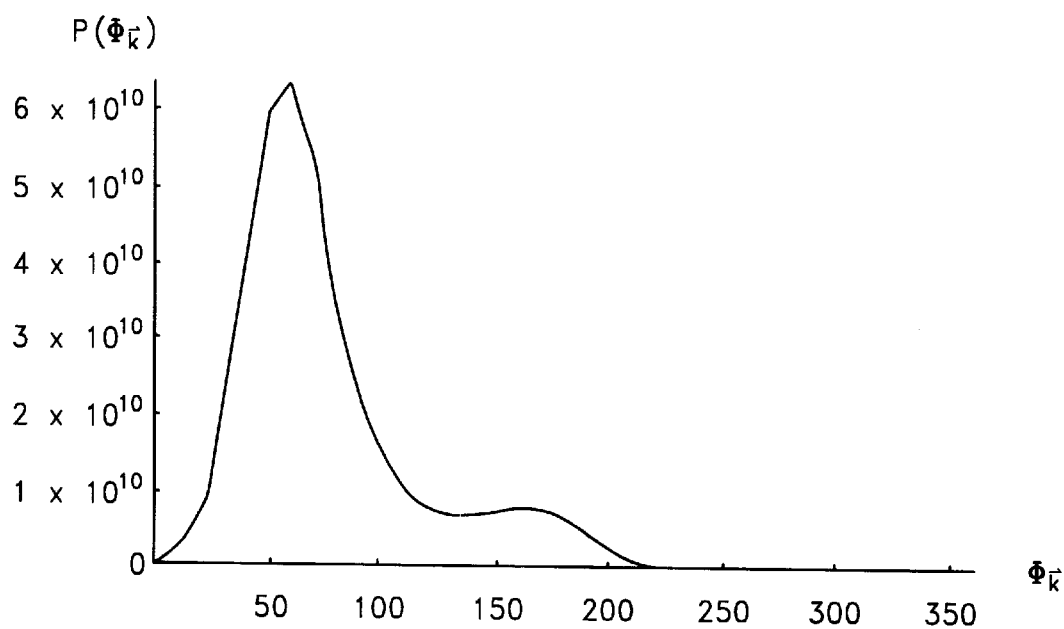

FIGS. 6A–6D and 7A–7D schematically illustrate an example of an embodiment of the present invention as applied to experimental data from the Protein Data Bank, code entry 3APP corresponding to x-ray diffraction data from penicillopepsin, as published by Sielecki and James in J. Mol. Bio., volume 163, page 299 (1983), which is incorporated by reference herein in its entirety. FIGS. 6A–6C schematically illustrate the phase probability distributions for the $\vec{k}=(9, 3, 0)$, $-\vec{h}=(-7, -1, 0)$, and $\vec{k}-\vec{h}=(2, 2, 0)$ reciprocal lattice vectors, respectively. The original phase probability distribution for the reciprocal lattice vector $\vec{k}$ in FIG. 6A is bimodal with a first peak mode centered at approximately 50 degrees and a second peak mode centered at approximately 210 degrees with an intensity approximately equal to that of the first peak. The probability distributions for the structure factor phases for the reciprocal lattice vectors $-\vec{h}$ and $\vec{k}-\vec{h}$ in FIGS. 6B and 6C respectively are substantially unimodal. As can be seen in the resultant phase probability distribution for the reciprocal lattice vector $\vec{k}$ in FIG. 6D, the intensity of the second peak mode has nearly disappeared, and the first peak has been sharpened somewhat.

Figure 8:
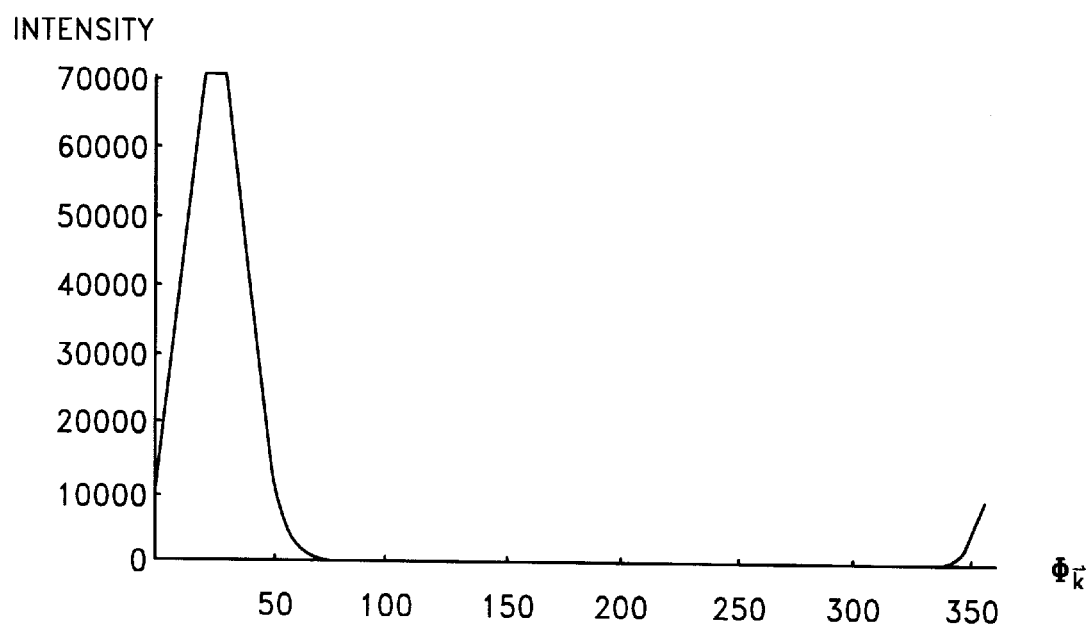
FIG. 8 schematically illustrates a "true" value of the phase obtained from density modification techniques corresponding to the reciprocal lattice vector $\vec{k}$.

For the purposes of comparison, density modification techniques can be used as an alternative method for refining the phase probability distribution. Density modification techniques have several sub-categories, based on assumptions such as non-crystallographic symmetry, solvent flattening, non-negativity of electron distributions, etc. A description of density modification techniques is provided by "Principles of Protein X-Ray Crystallography" by Jan Drenth, Chapter 8, pages 183–198, Springer-Verlag, New York, 1999, which is incorporated in its entirety by reference herein. The original phase probability distribution, illustrated in FIG. 6A, has a centroid at 129 degrees (far away from the value obtained from the density modification technique of 56 degrees) and a FOM value of 0.19. However, the resultant phase probability distribution, illustrated in FIG. 6D, has a centroid at 76 degrees (closer to the density modification value of 56 degrees) and a FOM value of 0.80. Therefore, the resultant phase probability distribution for the reciprocal lattice vector $\vec{k}$ has a structure factor phase ambiguity which is smaller than that of the original phase probability distribution for the reciprocal lattice vector $\vec{k}$. In addition, the centroid of the resultant phase probability distribution for $\vec{k}=(9, 3, 0)$ is in better agreement with that of the phase obtained from the density modification technique, which is schematically illustrated in FIG. 8.

Figure 7A:
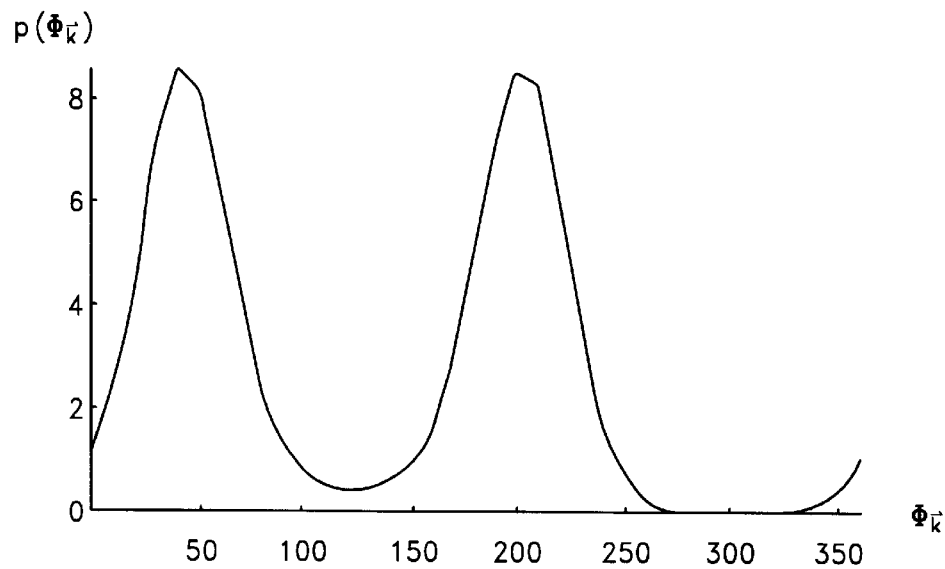
FIGS. 7A–7D schematically illustrate an example of an embodiment of the present invention as applied to certain reflections of experimental data.
Figure 7B:
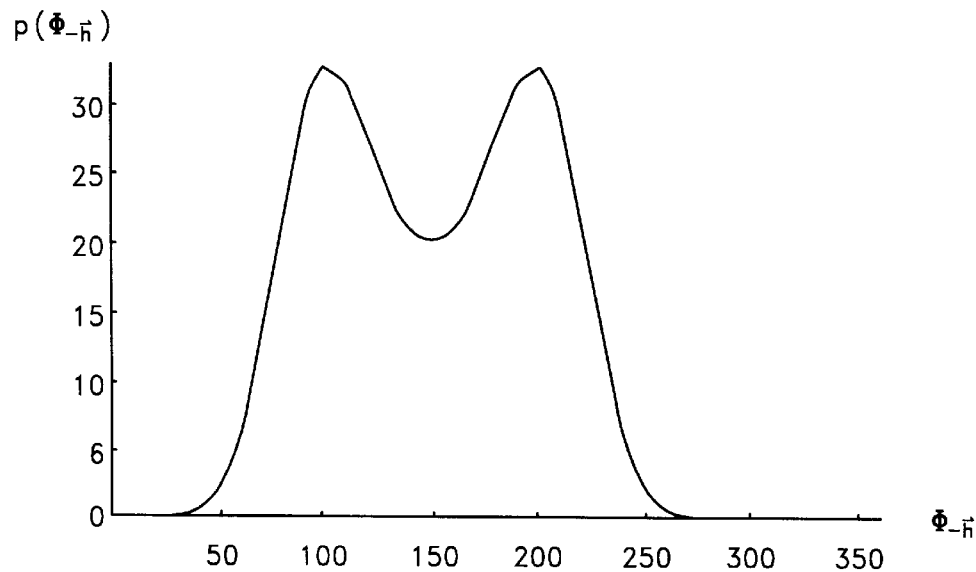
Figure 7C:
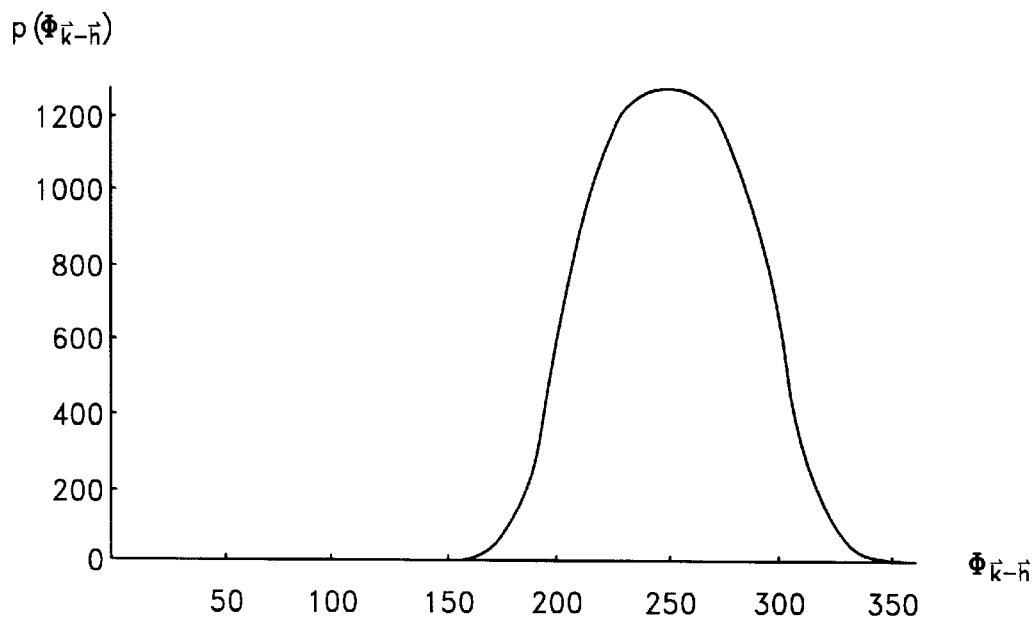
Figure 7D:
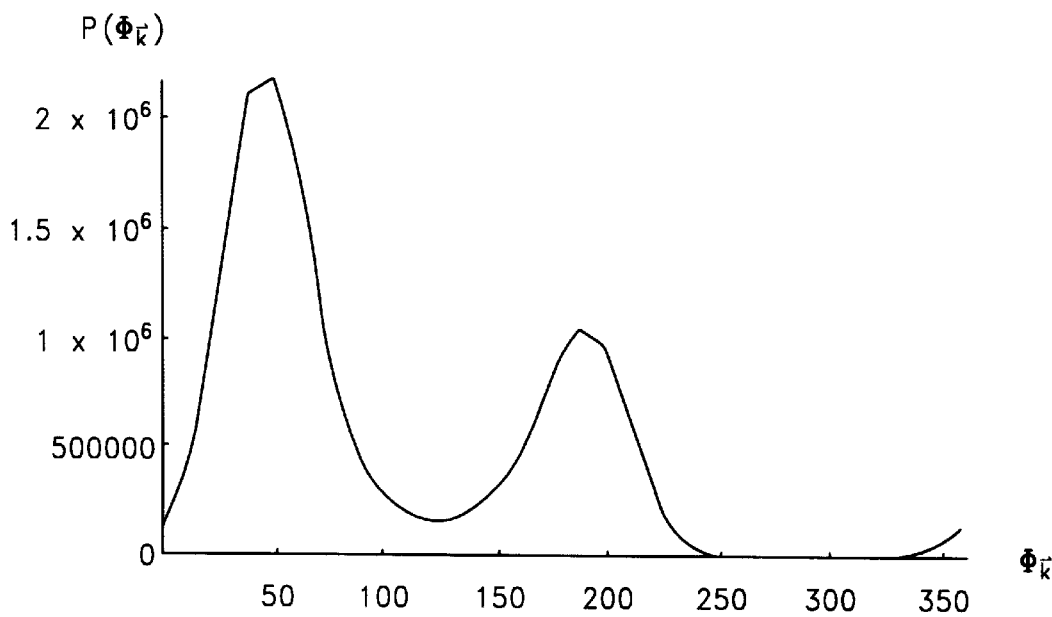

Similarly, FIGS. 7A–7C schematically illustrate the phase probability distributions for the $\vec{k}=(9, 3, 0)$, $-\vec{h}=(-5, -1, 0)$, and $\vec{k}-\vec{h}=(4, 2, 0)$ reciprocal lattice vectors, respectively. However, the phase probability distribution for the reciprocal lattice vector $-\vec{h}$ in FIG. 7B is substantially bimodal while the phase probability distribution for the $\vec{k}-\vec{h}$ in FIG. 7C is substantially unimodal but broad. As can be seen in the resultant phase probability distribution for the reciprocal lattice vector $\vec{k}$ in FIG. 7D, the intensity of the second peak mode still exists but has been reduced as compared to the intensity of the first peak, and the first peak has been sharpened somewhat.

The original phase probability distribution, illustrated in FIG. 7A, has a centroid at 129 degrees (far away from the value obtained from the density modification technique of 56 degrees) and a FOM value of 0.19. However, the resultant phase probability distribution, illustrated in FIG. 7D, has a centroid at 98 degrees (closer to the density modification value of 56 degrees) and a FOM value of 0.43. Therefore, the resultant phase probability distribution for the reciprocal lattice vector $\vec{k}$ has a structure factor phase ambiguity which is smaller than that of the original phase probability distribution for the reciprocal lattice vector $\vec{k}$. Again, the centroid of the resultant phase probability distribution for $\vec{k}=(9, 3, 0)$ is in better agreement with that of the phase obtained from density modification technique, which is schematically illustrated in FIG. 8.

Figure 9A:
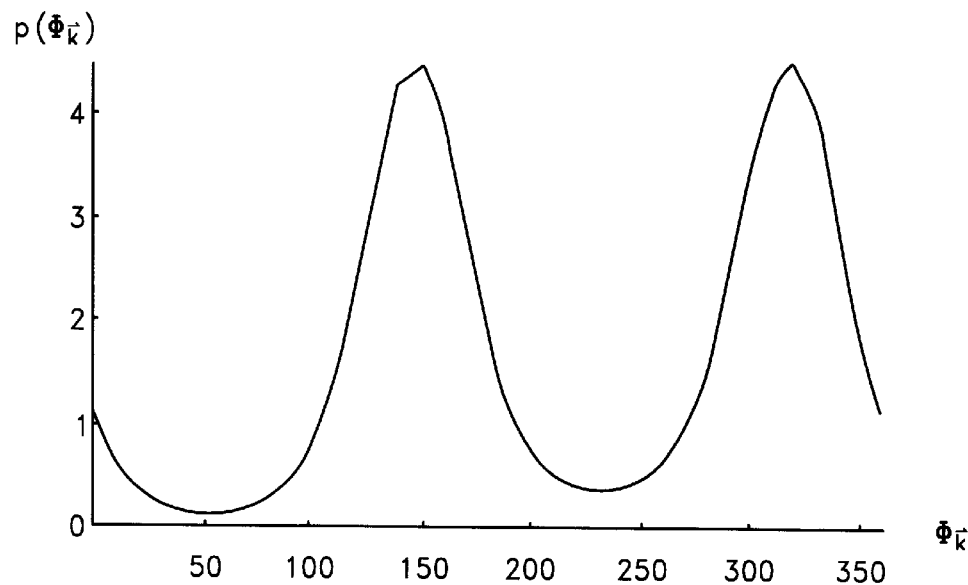
FIGS. 9A–9D schematically illustrate an example of an embodiment of the present invention as applied to certain reflections of experimental data.
Figure 9B:
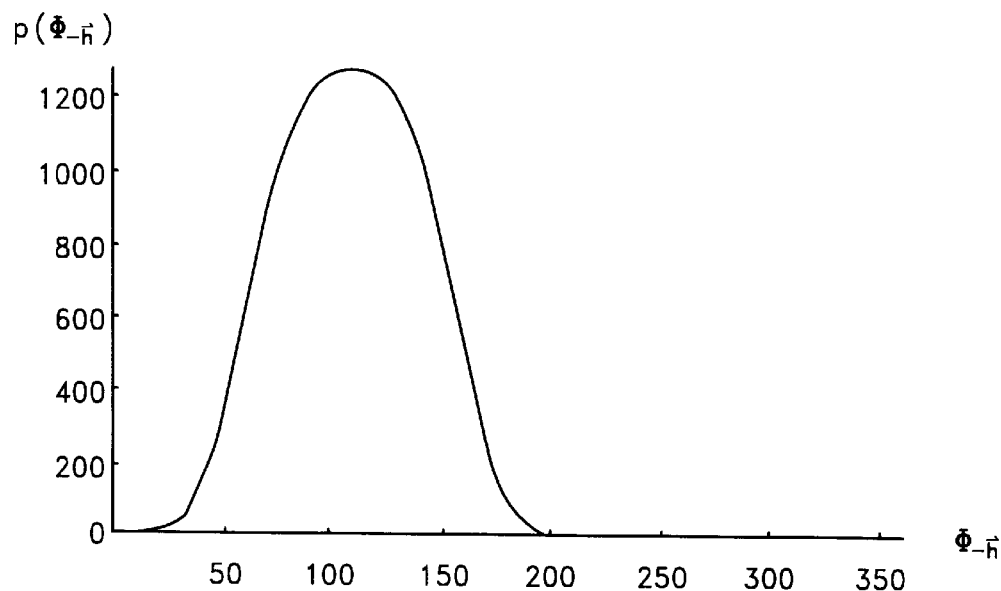
Figure 9C:
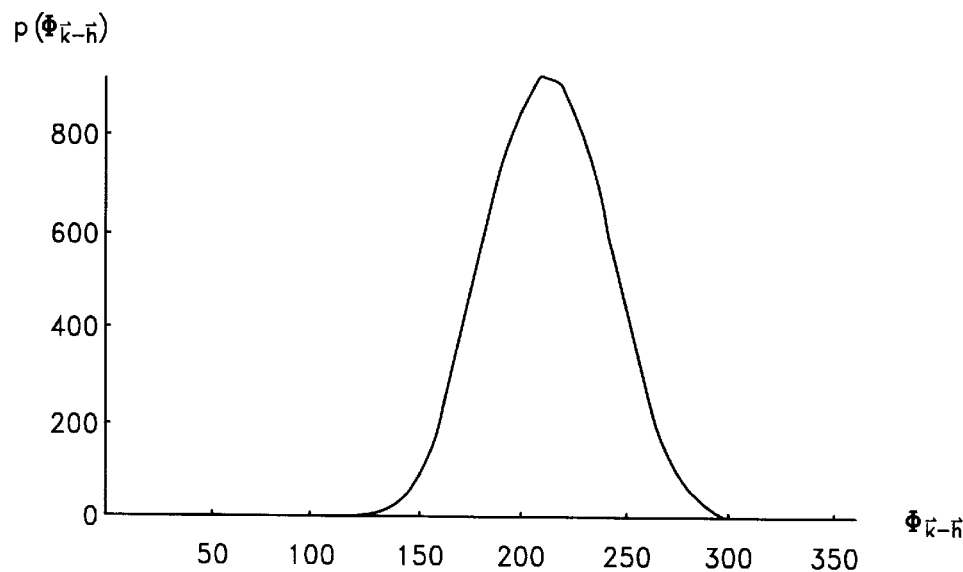
Figure 9D:
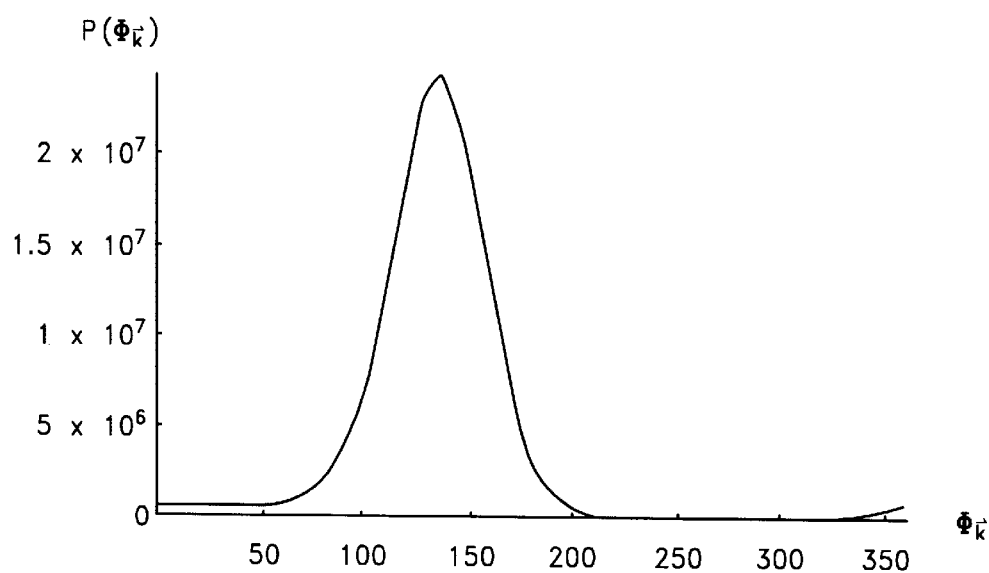

FIGS. 9A–9C schematically illustrate the phase probability distributions for the $\vec{k}=(6, 4, 0)$, $-\vec{h}=(-4, -2, 0)$, and $\vec{k}-\vec{h}=(2, 2, 0)$ reciprocal lattice vectors, respectively. The original phase probability distribution for the reciprocal lattice vector $\vec{k}$ in FIG. 9A is bimodal with a first peak mode centered at approximately 150 degrees and a second peak mode centered at approximately 315 degrees with an intensity approximately equal to that of the first peak. The probability distributions for the structure factor phases for the reciprocal lattice vectors $\vec{k}$ and $-\vec{h}$ in FIGS. 9B and 9C respectively are substantially unimodal, but broad. As can be seen in the resultant phase probability distribution for the reciprocal lattice vector $\vec{k}$ in FIG. 9D, the intensity of the second peak mode has been eliminated as compared to the intensity of the first peak, and the first peak has been sharpened somewhat.

Figure 9E:
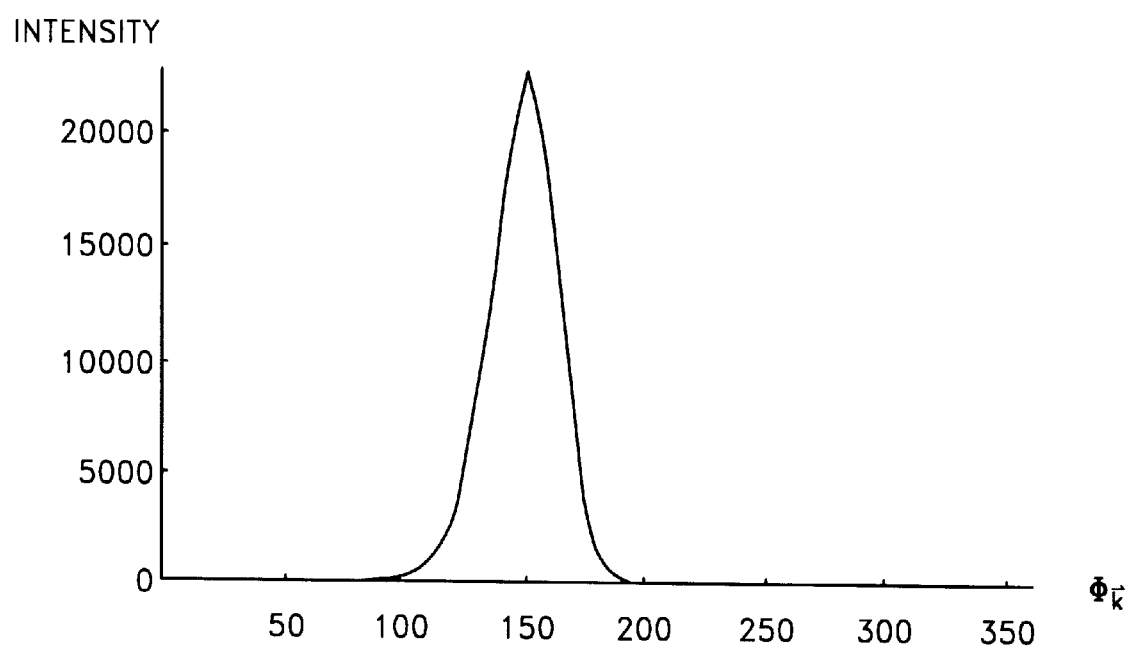
FIG. 9E schematically illustrates a "true" value of the phase obtained from density modification techniques corresponding to the reciprocal lattice vector $\vec{k}$.

The original phase probability distribution, illustrated in FIG. 9A, has a centroid at 220 degrees (far away from the value obtained from the density modification technique of 148 degrees) and a FOM value of 0.074. However, the resultant phase probability distribution, illustrated in FIG. 9D, has a centroid at 136 degrees (closer to the density modification value of 148 degrees) and a FOM value of 0.88. Therefore, the resultant phase probability distribution for the reciprocal lattice vector $\vec{k}$ has a structure factor phase ambiguity which is smaller than that of the original phase probability distribution for the reciprocal lattice vector $\vec{k}$. The centroid of the resultant phase probability distribution for $\vec{k}=(6, 4, 0)$ is in better agreement with that of the phase obtained from the density modification technique, as schematically illustrated in FIG. 9E.

Figure 10A:
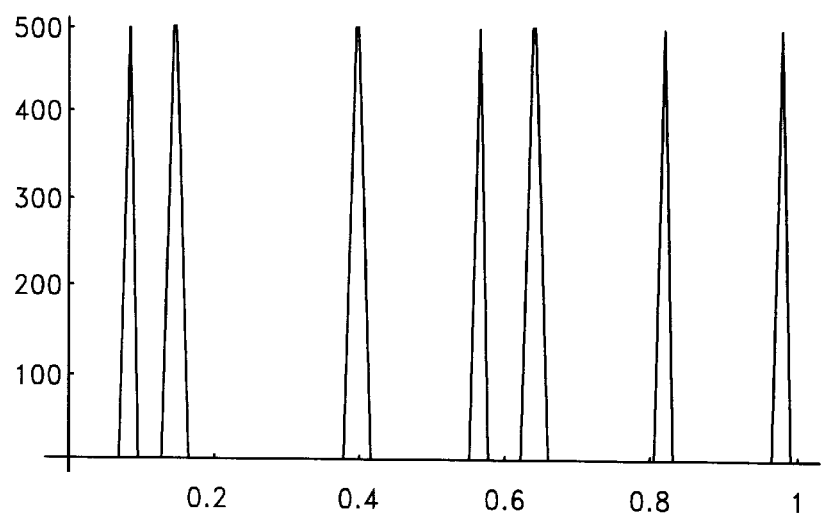
FIG. 10A schematically illustrates an artificial one-dimensional electron distribution composed of ten randomly positioned atoms.
Figure 10B:
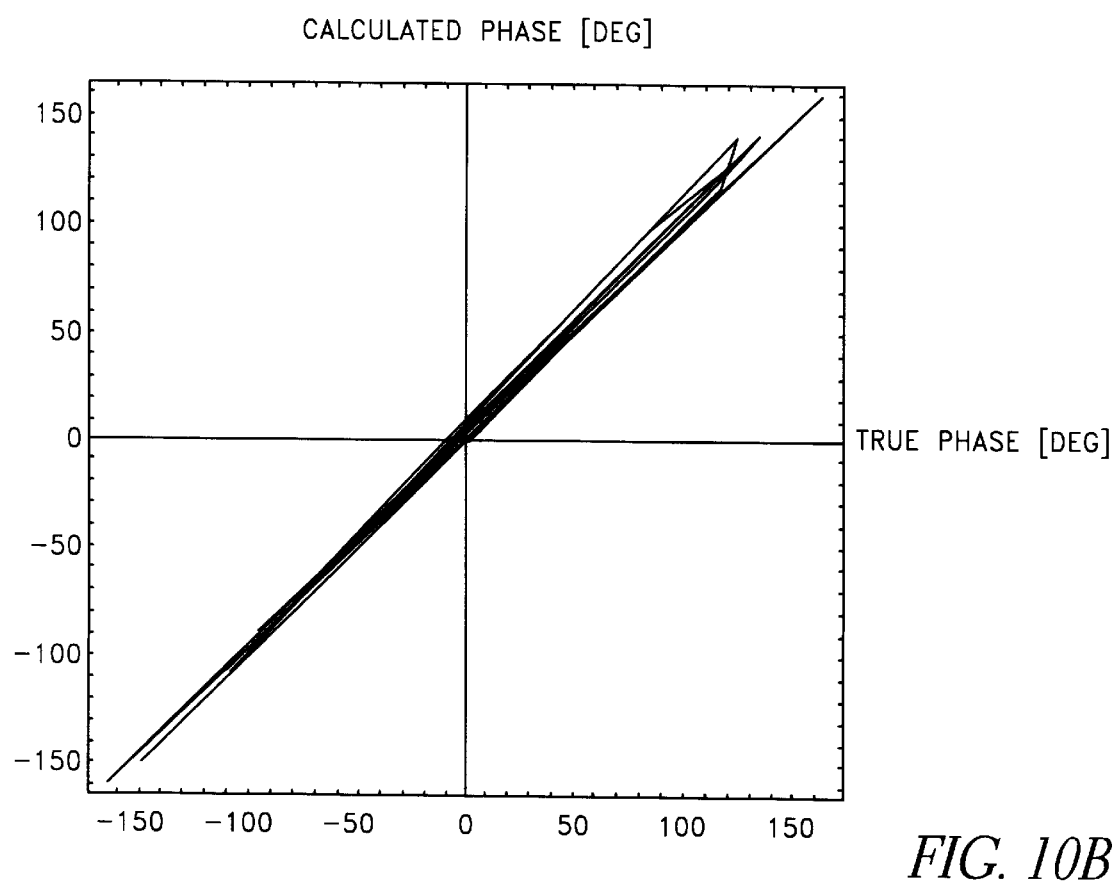
FIG. 10B schematically illustrates the correlation between the "calculated" structure factor phases produced by one embodiment of the present invention and the "true" structure factor phases computed from the electron distribution of FIG. 10A.

As a further example of an embodiment of the present invention, an artificial one-dimensional electron distribution composed of 10 randomly positioned atoms, as schematically illustrated in FIG. 10A, was used to compute the corresponding structure factors, and then to back-compute the electron distribution from the structure factors. All scattering factors were set equal to one, as well as the temperature factors and occupancies. The structure factors were also used in conjunction with the tangent formula of Equation 4 for comparison. FIG. 10B schematically illustrates the correlation between the "calculated" structure factor phases produced by the tangent formula used by an embodiment of the present invention and the "true" structure factor phases computed from the electron distribution. As can be seen from FIG. 10B, the embodiment of the present invention yielded structure factor phases which had a correlation with the true phases of nearly one.

Figure 10C:
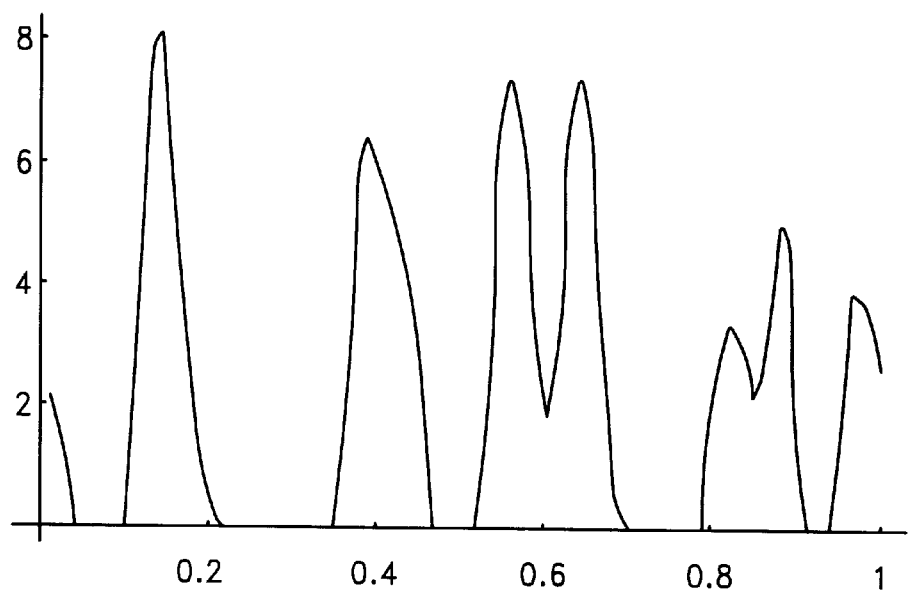
FIG. 10C schematically illustrates the electron distribution calculated from the set of structure factor phases from one embodiment of the present invention.
Figure 10D:
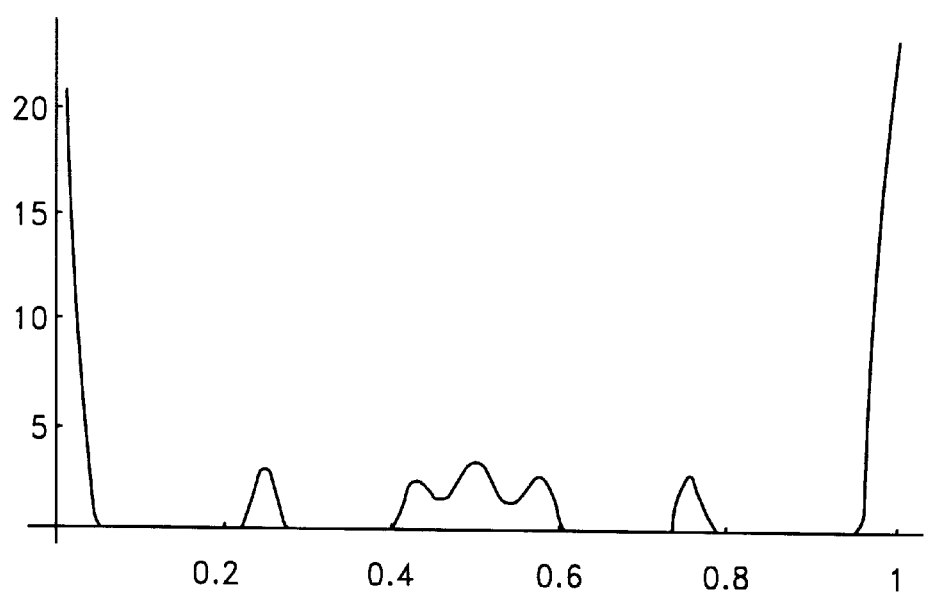
FIG. 10D schematically illustrates the electron distribution calculated from the structure factors with random phases.

The subset of low-order structure factor phases from the embodiment of the present invention were then used to calculate the electron distribution, as schematically illustrated in FIG. 10C. In calculating the phase probability distribution of FIG. 10C, negative values for electron densities were excluded, which is a physical constraint. Since the phase probability distribution of FIG. 10C was obtained from a truncated set of structure factors which are actually used in the Monte Carlo optimization, it has a reduced resolution as compared to FIG. 10A. A comparison of the original electron distribution of FIG. 10A and the resultant electron distribution of FIG. 10C reveals some correlation. This correlation is highlighted by comparing the original electron distribution of FIG. 10A with the calculated electron distribution of FIG. 10D, which schematically illustrates the electron distribution calculated from the structure factors with phases set to random numbers between −180 degrees and 180 degrees. FIG. 10D was also calculated by excluding negative values for electron densities. The reduction of correlation with the original electron distribution of FIG. 10A by ignoring the phases resulting from the embodiment of the present invention provides further support for the validity of the structure factor phases produced by embodiments of the present invention.

This invention may be embodied in other specific forms without departing from the essential characteristics as described herein. The embodiments described above are to be considered in all respects as illustrative only and not restrictive in any manner. The scope of the invention is indicated by the following claims rather than by the foregoing description. Any and all changes which come within the meaning and range of equivalency of the claims are to be considered within their scope.

What is claimed is:

1. A method of reducing structure factor phase ambiguity corresponding to a selected reciprocal lattice vector, the method comprising:

generating an original phase probability distribution corresponding to a selected structure factor phase of the selected reciprocal lattice vector, the original phase probability distribution comprising a first structure factor phase ambiguity;

combining the original phase probability distribution with a plurality of phase probability distributions of a plurality of structure factor phases of other reciprocal lattice vectors using a phase equation or inequality, the phase equation or inequality defining a mathematical relationship between the selected structure factor phase of the selected reciprocal lattice vector and the plurality of structure factor phases of other reciprocal lattice vectors; and producing a resultant phase probability distribution for the selected structure factor phase of the selected reciprocal lattice vector, the resultant phase probability distribution comprising a second structure factor phase ambiguity which is smaller than the first structure factor phase ambiguity.

2. The method of claim 1, wherein the original phase probability distribution is substantially bimodal.

3. The method of claim 1, wherein the resultant phase probability distribution is substantially unimodal.

4. The method of claim 1, wherein the resultant phase probability distribution is weighted more strongly to a correct phase than is the original phase probability distribution.

5. The method of claim 1, wherein the original phase probability distribution is generated by single isomorphous replacement, single anomalous dispersion, multiple isomorphous replacement, or multiple anomalous dispersion.

6. The method of claim 1, wherein the phase equation or inequality is the phase addition equation.

7. A method of defining a structure factor phase for a reflection derived from x-ray crystallography data, the method comprising:

generating a first probability distribution for the structure factor phase of the reflection;

generating two or more additional probability distributions for the structure factor phases of other reflections;

identifying a relationship between the structure factor phase for the reflection and the structure factor phases of the other reflections; and calculating a composite probability distribution for the structure factor phase of the reflection, whereby the composite probability distribution is derived from the first probability distributions for the structure factor phase of the reflection and the two or more additional probability distributions for the structure factor phases of the other reflections.

8. The method of claim 7, wherein the first probability distribution is defined by a set of Hendrickson-Lattman coefficients.

9. The method of claim 8, wherein the set of Hendrickson-Lattman coefficients are generated by single isomorphous replacement, single anomalous dispersion, multiple isomorphous replacement, or multiple anomalous dispersion.

10. The method of claim 7, wherein the first probability distribution is substantially bimodal.

11. The method of claim 7, wherein the composite probability distribution is substantially unimodal.

12. The method of claim 7, wherein the relationship between the structure factor phase for the reflection and the structure factor phases for the other reflections is additive.

13. The method of claim 12, wherein the relationship is given by the phase addition equation.

14. A computer readable medium having instructions stored thereon which cause a general purpose computer to perform a method of reducing structure factor phase ambiguity corresponding to a selected reciprocal lattice vector, the method comprising:

generating an original phase probability distribution corresponding to a selected structure factor phase of the selected reciprocal lattice vector, the original phase probability distribution comprising a first structure factor phase ambiguity;

combining the original phase probability distribution with a phase equation or inequality, the phase equation or inequality defining a mathematical relationship between the selected structure factor phase of the selected reciprocal lattice vector and a set of structure factor phases of other reciprocal lattice vectors; and producing a resultant phase probability distribution for the selected structure factor phase of the selected reciprocal lattice vector, the resultant phase probability distribution comprising a second structure factor phase ambiguity which is smaller than the first structure factor phase ambiguity.

15. A computer-implemented x-ray crystallography analysis system comprising:

an original phase probability distribution generator for generating an original phase probability distribution corresponding to a selected structure factor phase of the selected reciprocal lattice vector, the original phase probability distribution comprising a first structure factor phase ambiguity;

a combination module for combining the original phase probability distribution with a phase equation or inequality, the phase equation or inequality defining a mathematical relationship between the selected structure factor phase of the selected reciprocal lattice vector and a set of structure factor phases of other reciprocal lattice vectors; and a resultant phase probability distribution producer for producing a resultant phase probability distribution for the selected structure factor phase of the selected reciprocal lattice vector, the resultant phase probability distribution comprising a second structure factor phase ambiguity which is smaller than the first structure factor phase ambiguity.

16. A computer-implemented x-ray crystallography analysis system comprising:

a means for retreiving a first phase probability distribution corresponding to a selected structure factor phase of a selected reciprocal lattice vector;

a means for retreiving a plurality of second phase probability distributions corresponding to other structure factor phases of other reciprocal lattice vectors; and a means for combining the first phase probability distribution and plurality of second phase probability distributions so as to produce a resultant phase probability distribution for the selected structure factor phase of the selected reciprocal lattice vector.

17. A method of refining x-ray diffraction data, the method comprising combining structure factor phase probability distributions for different reciprocal lattice vectors so that the structure factor phase probability distribution for at least one of the reciprocal lattice vectors is more heavily weighted toward a phase value.

* * * * *